US010022043B2

(12) United States Patent
Xue

(10) Patent No.: US 10,022,043 B2
(45) Date of Patent: Jul. 17, 2018

(54) SHORTENED SLIT LAMP MICROSCOPE

(71) Applicant: Haixin Xue, Lexington, MA (US)

(72) Inventor: Haixin Xue, Lexington, MA (US)

( * ) Notice: Subject to any disclaimer, the term of this patent is extended or adjusted under 35 U.S.C. 154(b) by 138 days.

(21) Appl. No.: 14/757,712

(22) Filed: Dec. 23, 2015

(65) Prior Publication Data

US 2016/0374549 A1    Dec. 29, 2016

Related U.S. Application Data

(60) Provisional application No. 62/183,928, filed on Jun. 24, 2015.

(51) Int. Cl.
*A61B 3/10* (2006.01)
*A61B 3/00* (2006.01)
*A61B 3/135* (2006.01)

(52) U.S. Cl.
CPC .......... *A61B 3/0083* (2013.01); *A61B 3/0008* (2013.01); *A61B 3/135* (2013.01); *A61B 3/0075* (2013.01)

(58) Field of Classification Search
CPC ......... A61B 3/00; A61B 3/0008; A61B 3/135; A61B 3/0075; A61B 3/13; A61B 3/0083; A61B 3/028; A61F 9/008; A61F 9/00821; A61H 1/0218
USPC ....... 351/156, 205, 206, 214, 221, 244, 245; 297/391, 392; 359/375, 381; 602/17, 36
See application file for complete search history.

(56) References Cited

U.S. PATENT DOCUMENTS

| 4,128,317 | A | 12/1978 | LeCover |
| 4,139,280 | A * | 2/1979 | Kohler .............. A61B 3/00 248/188.4 |
| 5,767,942 | A | 6/1998 | Doherty |
| D410,661 | S | 6/1999 | Wolf |
| 7,083,281 | B2 | 8/2006 | Yogesan |
| 7,329,003 | B2 | 2/2008 | Nicolini |
| 7,445,338 | B1 | 11/2008 | Beattie |
| 7,670,003 | B2 | 3/2010 | Kendrick |
| 7,736,002 | B2 | 6/2010 | Small |
| 7,819,528 | B1 | 10/2010 | Dudee |
| 8,573,777 | B1 | 11/2013 | Kendrick |
| 2002/0060778 | A1 * | 5/2002 | Su ............... A61F 9/008 351/206 |

(Continued)

OTHER PUBLICATIONS

Keeler, "Most Innovative—You Decide," Opticanonline.net.

*Primary Examiner* — Mustak Choudhury
(74) *Attorney, Agent, or Firm* — Hamilton, Brook, Smith & Reynolds, P.C.

(57) ABSTRACT

An eye examination device including eye examination optics for examining a patient's eyes. A chin rest assembly accepts the patient's head and maintains the patient's head in a fixed stable position. The chin rest assembly can comprise two spaced apart upright posts for securing to a table, with a forehead rest member being secured to the two upright posts at an upper end, and a chin rest member being secured to the two upright posts below the forehead rest member. The chin rest member can have a chin rest portion which extends forwardly relative to an upright plane extending between centers of the two upright posts and away from the eye examination optics, so that generally only a front of the patient's face coincides with the upright plane when the patient's head engages the chin rest portion.

11 Claims, 19 Drawing Sheets

(56) References Cited

U.S. PATENT DOCUMENTS

2006/0109424 A1* 5/2006 Nicolini .............. A61B 3/0083
351/244

* cited by examiner

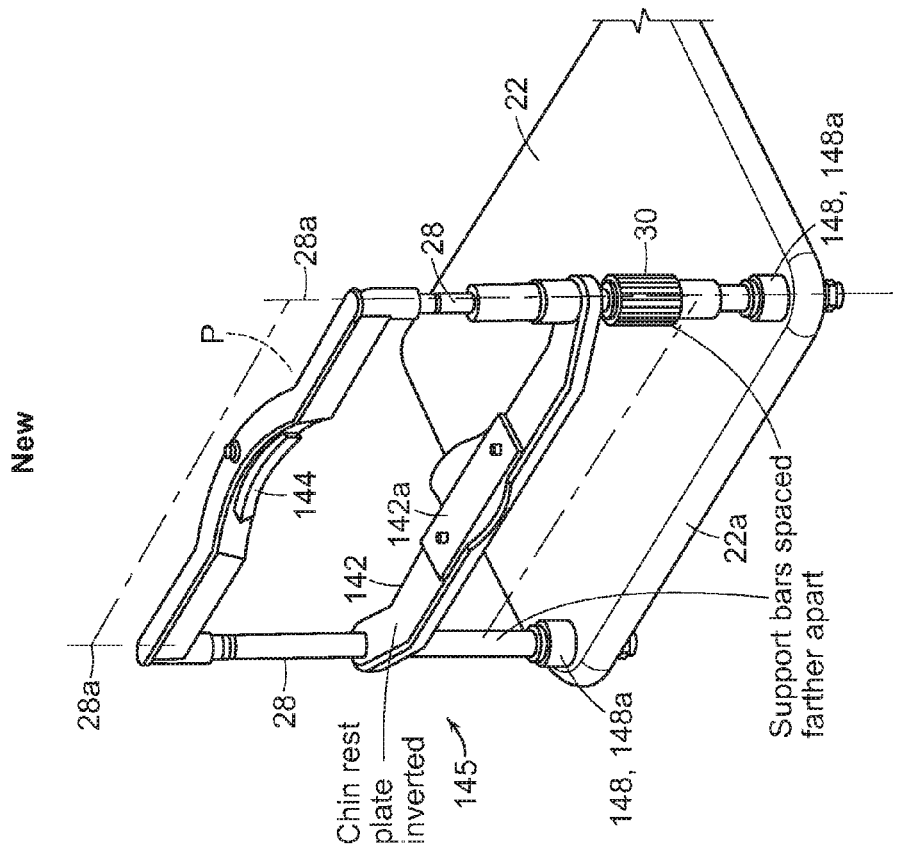
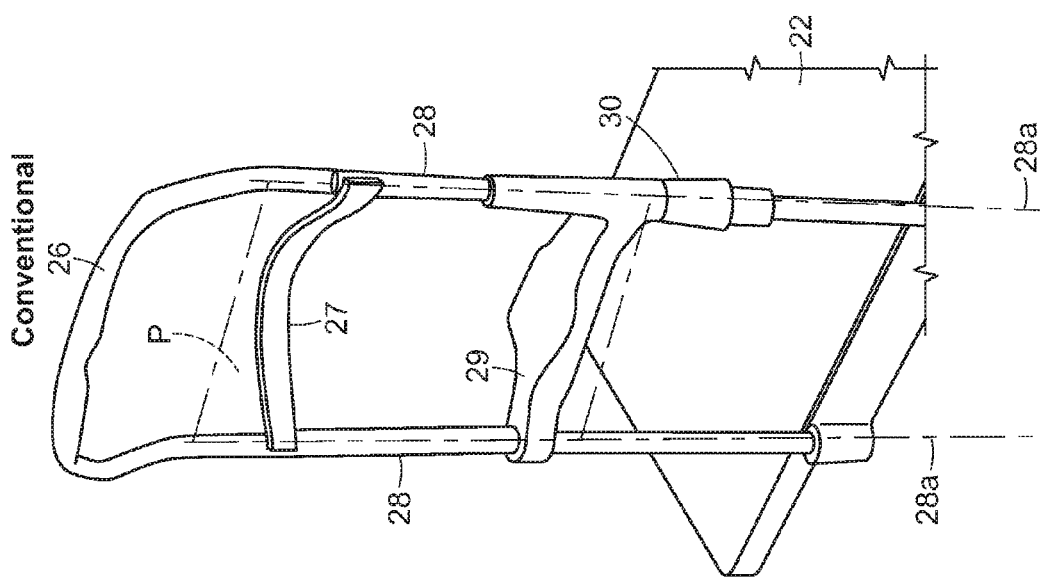
FIG. 12
FIG. 11

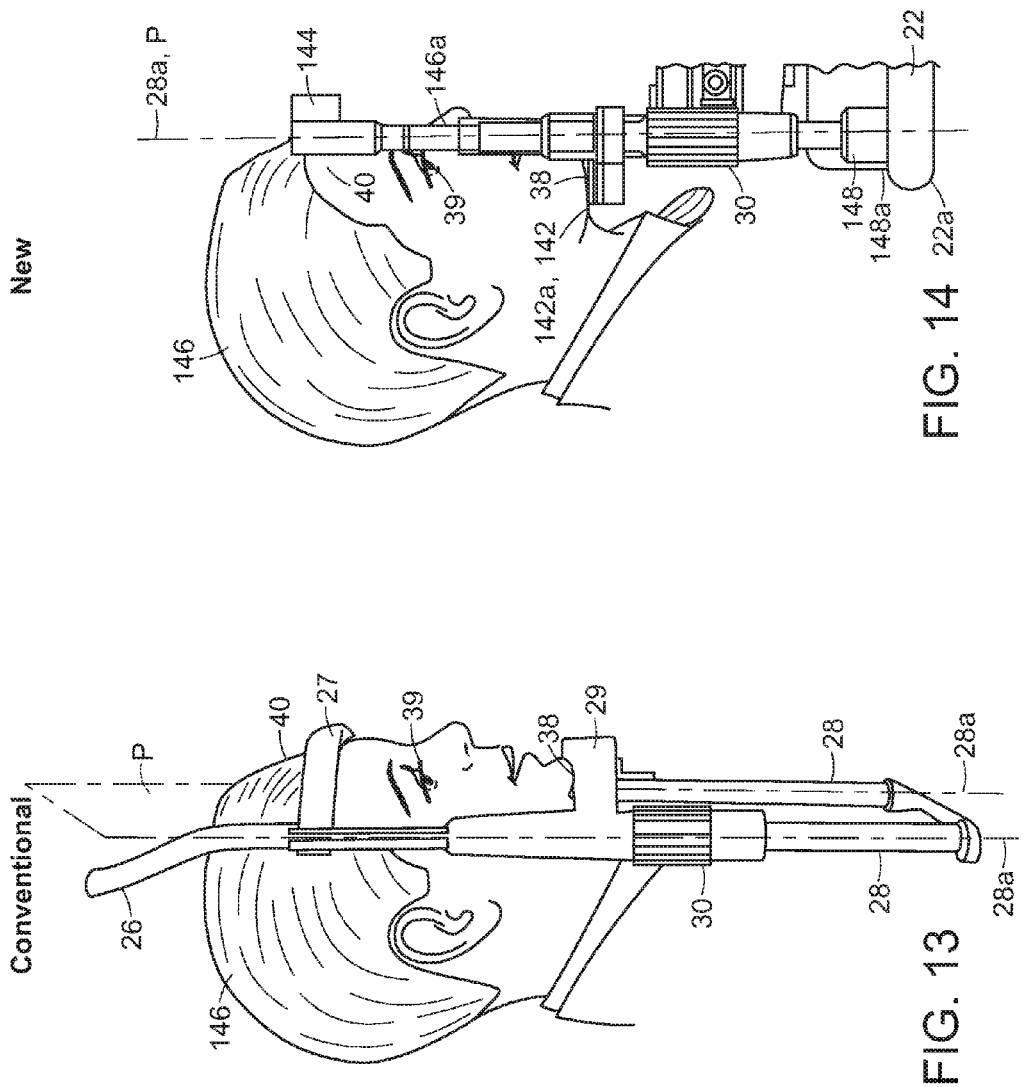

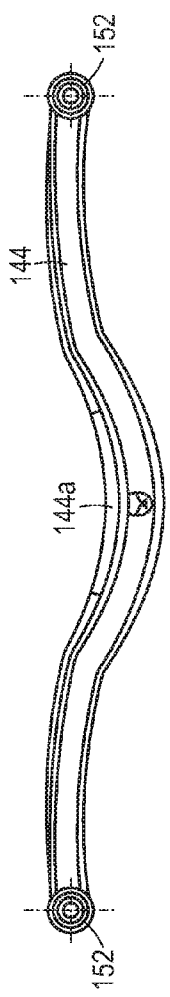
FIG. 18
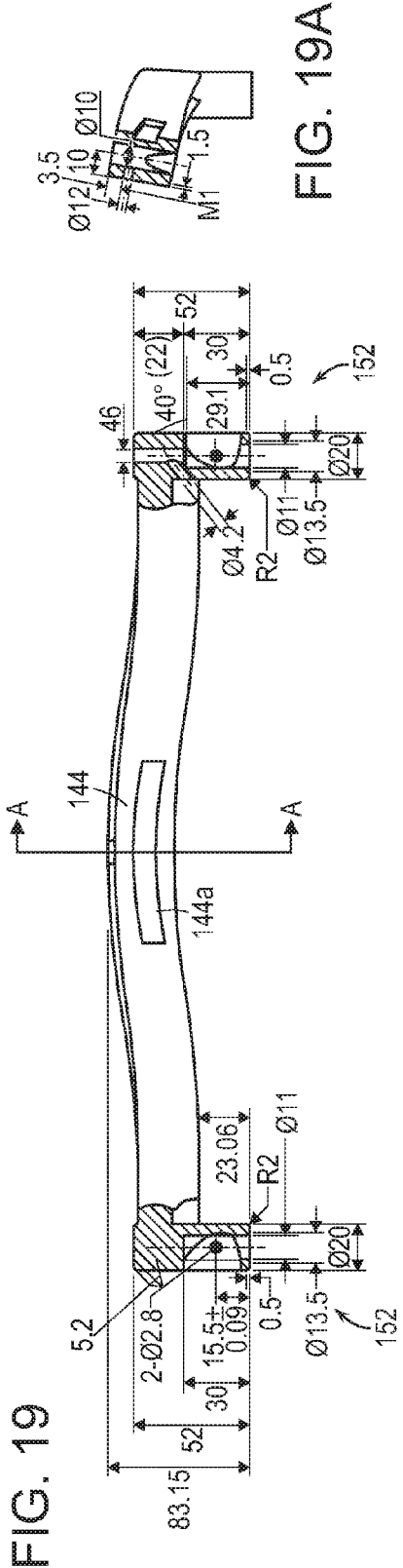
FIG. 19
FIG. 19A
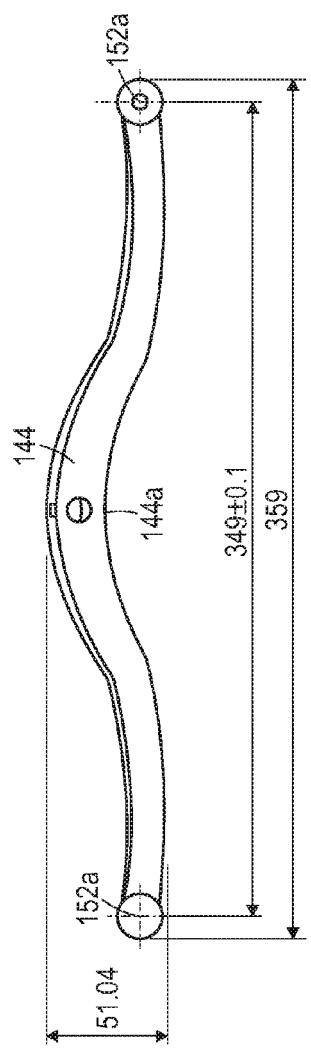
FIG. 20

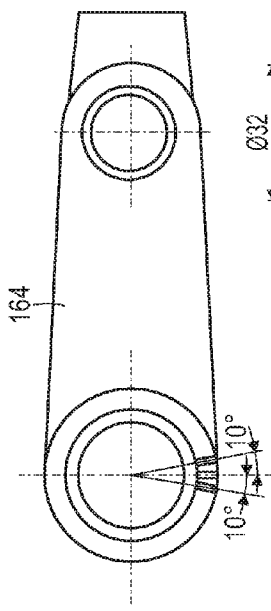
FIG. 24
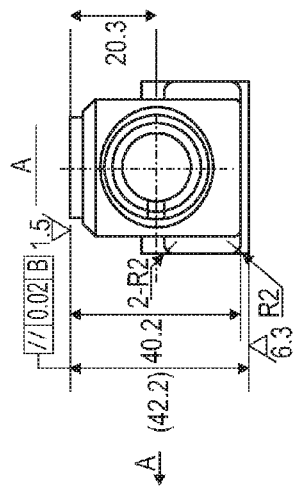
FIG. 26
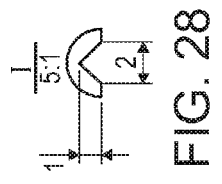
FIG. 28
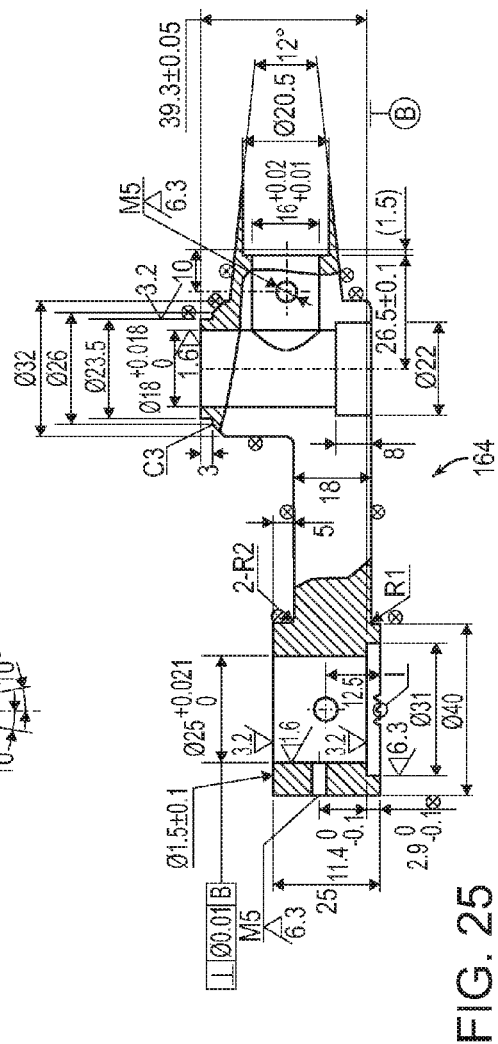
FIG. 25
FIG. 27

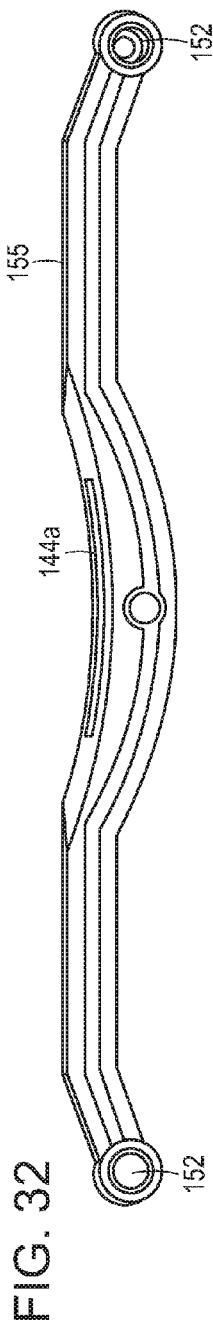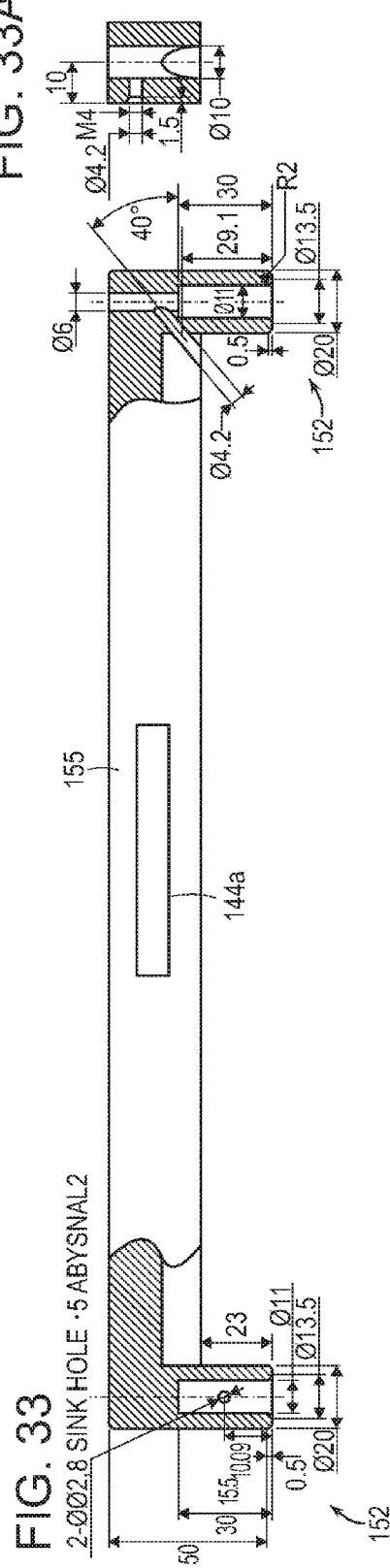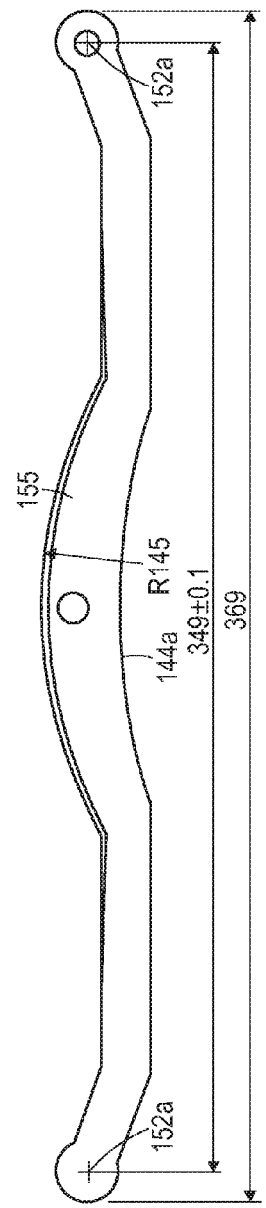

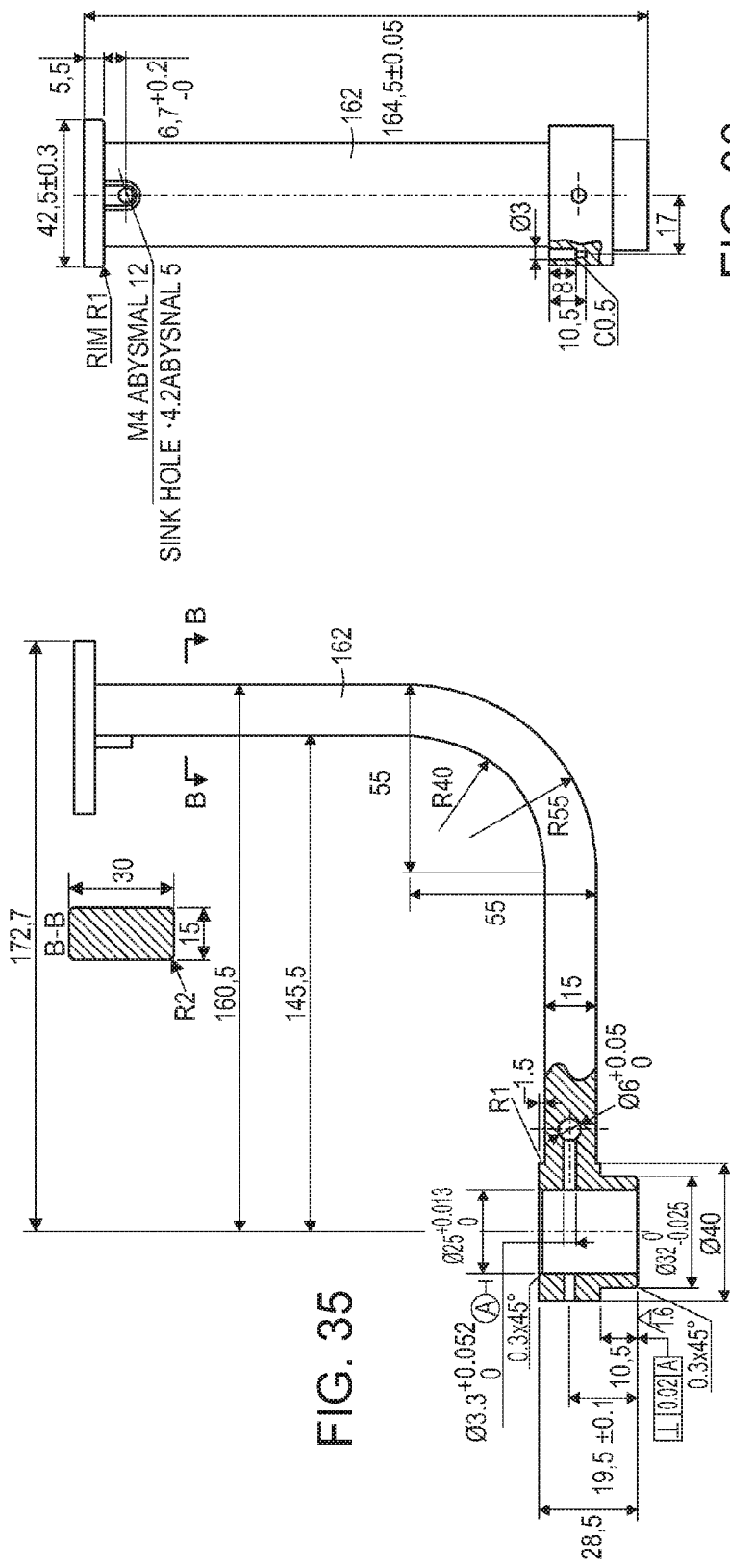
FIG. 35
FIG. 36
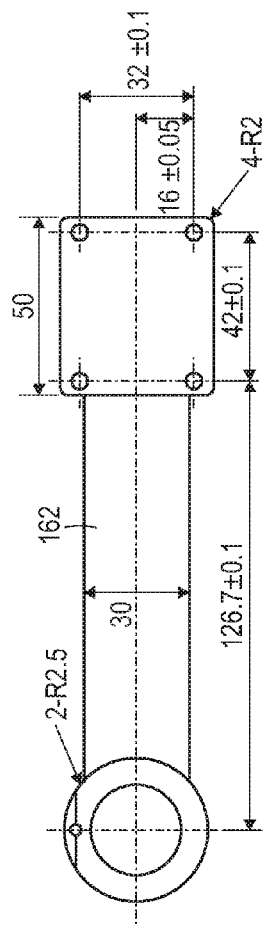
FIG. 37

SHORTENED SLIT LAMP MICROSCOPE

RELATED APPLICATION

This application claims the benefit of U.S. Provisional Application No. 62/183,928, filed on Jun. 24, 2015. The entire teachings of the above application are incorporated herein by reference.

BACKGROUND OF THE INVENTION

Conventional slit lamp microscopes (U.S. Pat. No. D410,661; Jun. 8, 1999; Wolf, Theodor) are placed on a movable tabletop and positioned between the patient and examiner. The parts of the slit lamp include a joystick base controlled by the examiner, movable arms supporting the light source and optical components, and a chin rest and forehead rest for the patient to place his or her chin and forehead against while leaning forward to be examined. The height of a conventional slit lamp typically positions the base at the stomach region of the average patient and the focal point of the optical components at the eyes. This is problematic when the patient body's shape and size falls outside of the average parameters or when the patient has limited body mobility, which can prevent the patient from being able to reach the chin and forehead rest while in a normal seated position.

More recently, slit lamp manufacturers and inventors have released or proposed modifications to the conventional slit lamp design in attempts to overcome the aforementioned problems, e.g. the handheld slit lamp (U.S. Pat. No. 5,767,942; Jun. 16, 1998; Doherty, Victor J.), portable slit lamp (U.S. Pat. No. 7,083,281; Aug. 1, 2006; Yogesan, Kanagasingam), suspended slit lamp (U.S. Pat. No. 7,736,002; Jun. 15, 2010; Small, Kent W.) and table-free slit lamp (U.S. Pat. No. 7,819,528; Oct. 26, 2010; Dudee, Jitander Singh). However, these prior modifications sacrifice important functions, features and usability of the conventional slit lamp. For example, the handheld and portable slit lamps currently available on the market only have one or two levels of magnification and generally require manual replacement of the ocular lenses to change between magnifications (versus up to five levels of magnification in a conventional slit lamp changeable via rotating drum), fewer filters than a conventional slit lamp, and inability to support many of the peripheral accessories available to conventional slit lamps for enhanced examination procedures (including, but not limited to, background illumination, wratten filtration, applanation tonometry, and specular microscopy); the suspended and table-free slit lamps have not yet been manufactured for the mass market, and as such are untested, but by the nature of their design are more challenging for the examiner to maneuver and operate than conventional slit lamps.

Typically, conventional slit lamp microscopes and associated chin rests used to examine a patient's eyes, are difficult to use for examining large or obese patients (for example over 300 pounds, or 200 pounds for a short person), due to the size and shape of the patient. Although a large or obese patient's head and body can be pushed forward and forced by a doctor's assistant into the chin rest and against the equipment, this can be uncomfortable or painful for the patient.

SUMMARY OF THE INVENTION

The present invention includes a shortened slit lamp microscope placed upon an elevated tabletop to bypass most of the patient's torso, allowing more direct access to the patient's chin and forehead for proper positioning for an eye examination.

The present invention can also provide a slit lamp microscope or eye examination device having a chin rest, which can be comfortably used with large or obese patients, including those over 300 pounds, and even 400 pounds and over. Embodiments of the eye examination device in the present invention can include eye examination optics for examining a patient's eyes. A chin rest assembly can accept the patient's head and hold or maintain the patient's head in a fixed stable position. The chin rest assembly can include two spaced apart upright posts for securing to a table. A forehead rest member can be secured to the two upright posts at an upper region or end. A chin rest member can be secured to the two upright posts below the forehead rest member. The chin rest member can have a chin rest portion which extends forwardly relative to an upright plane extending between centers of the two upright posts and away from the eye examination optics, so that generally at most, only a front of the patient's face coincides with the upright plane when the patient's head engages the chin rest portion.

In particular embodiments, the two upright posts can be spaced apart at least about 349 mm apart. The chin rest member can include a bar having two ends that are angled forwardly to extend the chin rest portion forwardly therebetween. The chin rest portion can be extended forwardly relative to the upright plane by at least about 38.76 or 38 mm. In some embodiments, the chin rest portion can extend forwardly relative to the upright plane from about 18, 30 or 38 mm to about 70 mm. Moving the chin rest portion forwardly from about 18, 30, or 38 mm to about 70 mm, can move the front or front plane of the patient's face forward or in front of the upright plane and the upright posts. The height of eye examination components including the eye examination optics mounted on top of the table can be shortened, so that body parts of the patient, including protruding, large, obstructing, interfering or obese body parts, can be positioned below the table during examination, in a generally non-interfering manner.

The eye examination components can include a joystick base mounted to the table. A central ocular arm having a horizontal bottom portion and an upright upper portion can be mounted on the joystick base. An optical assembly which can include eye examination eyepieces, can be mounted to the upright upper portion of the central ocular arm. An upright or vertical illumination tower having a light source can be mounted to the horizontal bottom portion of the central ocular arm and have a light reflecting mirror adjacently spaced apart from the optical assembly for reflecting light from the light source onto the patient's eye. The light reflecting mirror can be positioned above the table about 320 mm or 265 mm or less so that the table can be positioned above the body parts of the patient.

The present invention can also provide a chin rest assembly, for use with an eye examination device having eye examination optics for examining a patient's eyes. The chin rest assembly can accept the patient's head and maintain the patient's head in a fixed stable position. The chin rest assembly can include two spaced apart upright posts for securing to a table, with a forehead rest member being secured to the two upright posts at an upper region or end, and a chin rest member being secured to the two upright posts below the forehead rest member. The chin rest member can have a chin rest portion which extends forwardly relative to the upright plane extending between centers of the two upright posts and away from the eye examination optics, so that generally at most, only a front of the patient's face coincides with the upright plane when the patient's head engages the chin rest portion. The two upright posts can be spaced apart at least about 349 mm apart. The chin rest member can include a bar having two ends that are angled forwardly to extend the chin rest portion forwardly therebetween relative to the upright plane by at least about 18 mm.

The present invention can also provide an eye examination device including a table and eye examination optics for examining a patient's eyes mounted on top of the table. Eye examination components including the eye examination optics can have a shortened height above the table so that body parts of the patient, including protruding, large, interfering or obese body parts, can be positioned below the table during examination in a generally non-interfering manner. The eye examination components can include a joystick base mounted to the table. A central ocular arm can have a horizontal bottom portion and an upright upper portion mounted on the joystick base. An optical assembly can be mounted to the upright upper portion of the central ocular arm. An illumination tower having a light source can be mounted to the horizontal portion of the central ocular arm and have a light reflecting mirror adjacently spaced apart from the optical assembly for reflecting light from the light source onto the patient's eye. The light reflecting mirror can be positioned above the table about 320 mm or less so that the table can be positioned above the body parts of the patient.

The present invention can also provide a method of examining a patient's eyes including mounting eye examination optics on top of a table and examining the patient's eyes. The height of eye examination components including the eye examination optics can be shortened and mounted on top of the table, so that body parts of the patient, including protruding, large, interfering or obese body parts, can be positioned below the table in a generally non-interfering manner.

In particular embodiments, the eye examination components can be provided with a joystick base mounted to the table. A central ocular arm having a horizontal bottom portion and an upright upper portion can be mounted on the joystick base. An optical assembly can be mounted to the upright upper portion of the central ocular arm. An illumination tower having a light source can be mounted to the horizontal bottom portion of the central ocular arm and can have a light reflecting mirror adjacently spaced apart from the optical assembly for reflecting light from the light source onto the patient's eye. The light reflecting mirror can be positioned above the table about 320 mm or 265 mm or less so that the table can be positioned above the body parts of the patient. The patient's head can be accepted and maintained in a fixed stable position with a chin rest assembly. The chin rest assembly can include two spaced apart upright posts secured to the table. A forehead rest member can be secured to the two upright posts at an upper region or end, and a chin rest member can be secured to the two upright post below the forehead rest member. The chin rest member can have a chin rest portion which extends forwardly relative to an upright plane extending between centers of the two upright posts and away from the eye examination optics, so that generally at most, only a front of the patient's face coincides with the upright plane when the patient's head engages the chin rest portion. The two upright posts can be spaced at least about 349 mm apart. The chin rest member can be provided with a bar having two ends that are angled forwardly to extend the chin rest portion forwardly therebetween. The chin rest portion can be extended forwardly relative to the upright plane by at least about 38 mm. In some embodiments, the chin rest portion can extend forwardly relative to the upright plane from about 18, 30 or 38 mm to about 70 mm.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 11 is a front perspective view of a conventional chin rest assembly.

FIG. 12 is a front perspective view of an embodiment of a chin rest assembly in the present invention.

FIG. 13 is a side perspective view of a patient's head in the conventional chin rest assembly of FIG. 11.

FIG. 14 is a side view of a patient's head in the chin rest assembly of FIG. 12.

FIGS. 18, 19, 19A and 20 are bottom, front with portions in section, cross-sectional and top views, respectively, of an embodiment of a forehead rest in the present invention.

FIGS. 24, 25, 26, 27 and 28 are top, side with portions in section, end, bottom and enlarged detail views, respectively, of an embodiment of an illumination tower base in the present invention.

FIGS. 32, 33, 33A and 34 are bottom, front with portions in section, cross-sectional and top views, respectively, of another embodiment of a forehead rest in the present invention.

FIGS. 35, 36 and 37 are side with portions in section, front and top views, respectively, of another embodiment of a central ocular arm in the present invention.

DETAILED DESCRIPTION OF THE INVENTION

A description of example embodiments of the invention follows.

Figure 1:
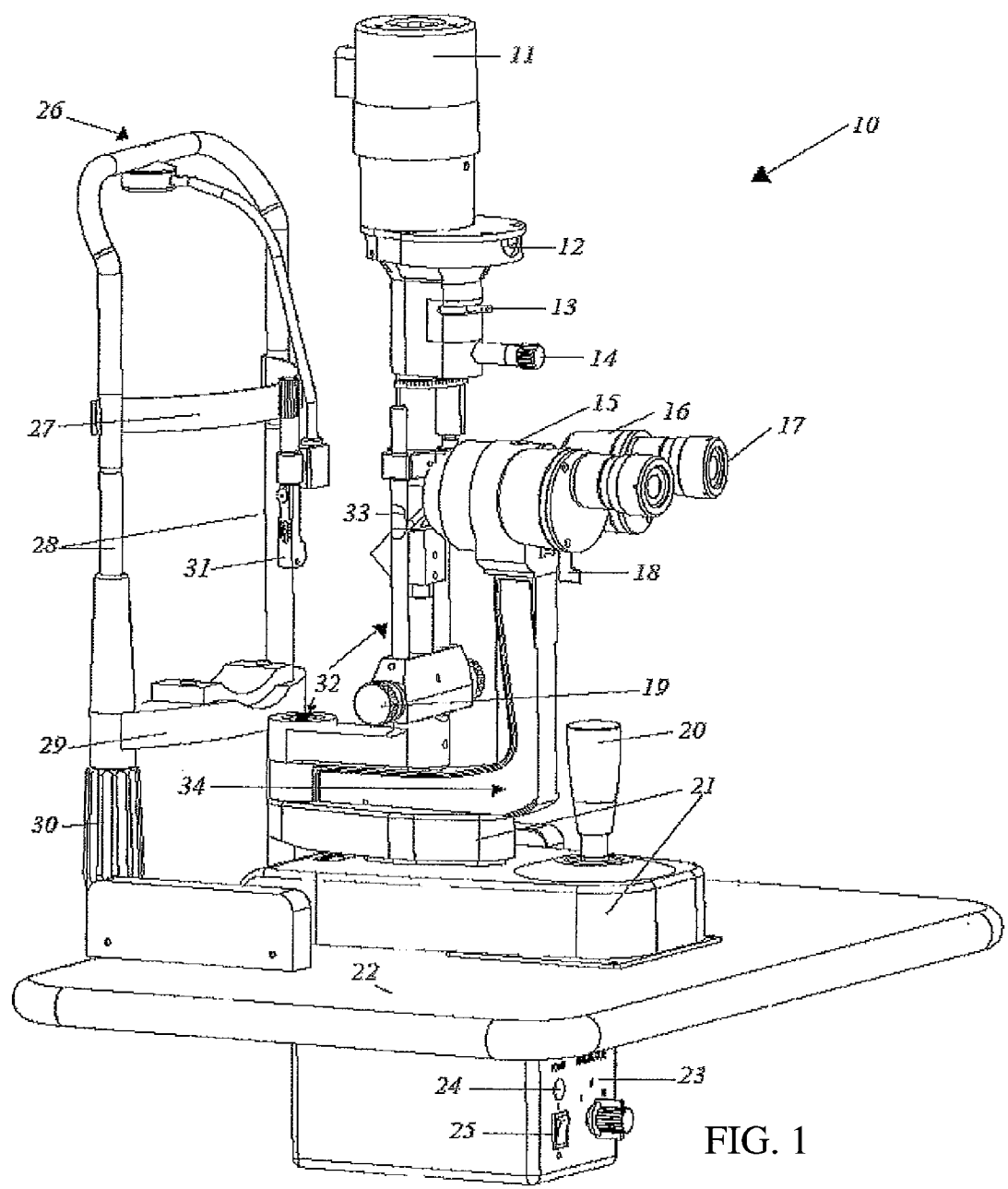
FIG. 1 is a perspective view of a shortened, elevated slit lamp within the present invention.

Referring now to the invention in more detail, in FIG. 1 there is shown a slit lamp microscope 10 which includes the lamp cap 11 with microscope light source, slit aperture display window 12, filter selection lever 13, slit aperture control knob 14, accessories mount 15, prism box 16, examiner's eyepiece 17, magnification changer 18, slit width control knob 19, joystick 20, joystick base 21, patient forehead and chin rest set 26, forehead strap 27, chin rest support bars 28, chin rest plate 29, chin rest elevation adjuster 30, fixation light 31, illumination tower 32, light reflecting mirror or member 33 and central ocular arm 34. There is also shown a tabletop 22 (which is connected to an adjustable instrument stand that is described below), power supply 23, power indicator light 24 and on/off switch 25.

In more detail, still referring to the invention of FIG. 1, the light reflecting mirror 33 shines a focused beam of light on a patient's eye (not shown) for the purpose of examination, the illumination tower 32 supports the lamp cap 11 which includes and houses the microscope's light source, slit aperture display window 12 which shows the current size of the light beam, filter selection lever 13 which controls the active filter, slit aperture control knob 14 which controls the height of the light beam, slit width control knob 19 which controls the width of the light beam, and the light reflecting mirror 33. The light cap 11 can in some embodiments be considered the microscope light source which directs light to the light reflecting mirror 33. The central ocular arm or member 34 supports the accessories mount 15 which can be used to mount peripheral examination tools, prism box 16 which adjusts the interpupillar distance for an examiner (not shown), examiner's eyepiece 17 which defines the image, and magnification changer 18 which controls the level of image magnification. The magnification changer 18, accessories mount 15, prism box 16 and examiner's eyepiece 17, can form or be part of an optical assembly, and can be mounted on the upright upper portion of the central ocular arm 34, which in turn is mounted on the joystick base 21. The illumination tower 32 with the light cap light source 11 can be upright and vertical, and can be mounted to the horizontal bottom portion of the central ocular arm 34. The joystick 20 and joystick base 21 is used by an examiner (not shown) to maneuver the slit lamp microscope 10 forward, back, left, right, up and down. The tabletop 22 supports the slit lamp microscope 10, power supply 23, power indicator light 24 and on/off switch 25 which turns the microscope's light source on or off. The patient forehead and chin rest set 26, which includes the chin rest support bars 28, forehead strap 27, chin rest plate 29, chin rest elevation adjuster 30 and fixation light 31, is mounted to the tabletop 22; the forehead strap 27 and chin rest plate 29 support a patient's forehead and chin, respectively, when a patient (not shown) leans forward into the slit lamp microscope 10 for examination, and the chin rest elevation adjuster 30 is used to raise and lower the chin rest plate 29 for optimal positioning.

In further detail, still referring to FIG. 1, the distance (height) between the light reflecting mirror 33 and tabletop 22 can be shortened to about 320 mm (12.5 inches) or less or about 265 mm (10.4 inches) or less during construction, which in some embodiments, can be about 260 mm (10.2 inches), or about 250-255 mm (9.8-10 inches). This shortening may be achieved via a combination of modifications to any or all mechanical parts of the slit lamp, including, without limitation, shrinking, flattening or truncating the illumination tower 32, the central ocular arm 34, and/or the joystick base 21. Accordingly, the patient forehead and chin rest set 26 must be shortened to match the new height of the modified slit lamp, including, but not limited to, shrinking, flattening or truncating the chin rest support bars 28 and chin rest plate 29.

The construction details of the invention as shown in FIG. 1 may be made of metal, glass, plastic or wood.

Figure 2:
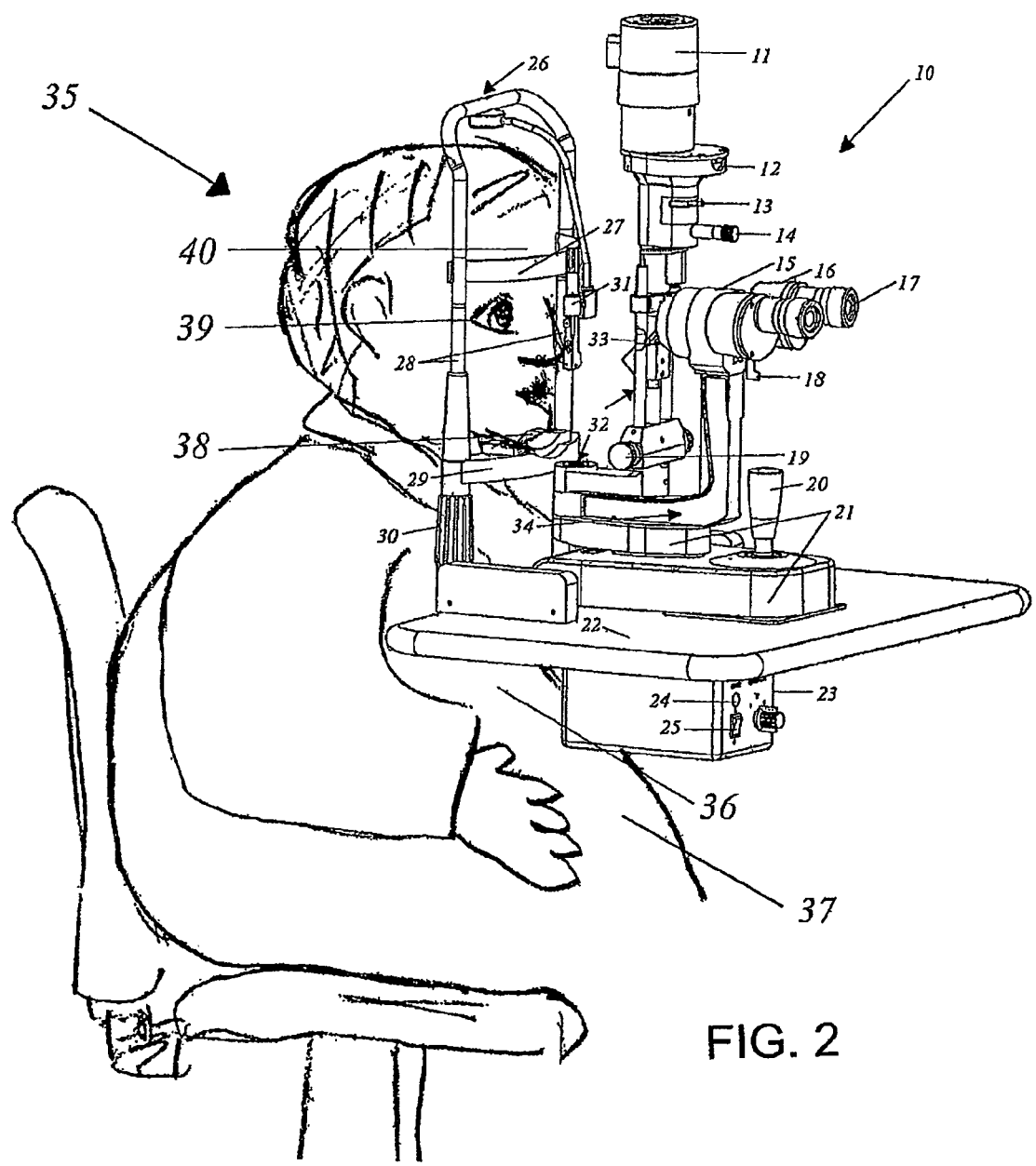
FIG. 2 is a perspective view of a patient seated at the shortened, elevated slit lamp of FIG. 1.

Referring now to FIG. 2, there is shown the position of the slit lamp microscope 10 relative to a seated patient 35, including the patient's upper chest region 36, lower stomach region 37, chin 38, eye 39 and forehead 40.

In more detail, still referring to FIG. 2, the tabletop 22 is positioned level with the patient's upper chest region 36, thereby bypassing the lower stomach region 37 which might otherwise cause an obstruction. In the position shown, the patient is now able to comfortably reach and place his or her chin 38 on the chin rest plate 29 and his or her forehead 40 against the forehead strap 27.

In more detail, still referring to the invention of FIG. 2, the distance between the patient's eye 39 and upper chest region 36 where it meets the tabletop 22 can be about 320 mm or less or about 265 mm or less, such as about 260 mm or about 250-255 mm.

Figure 3:
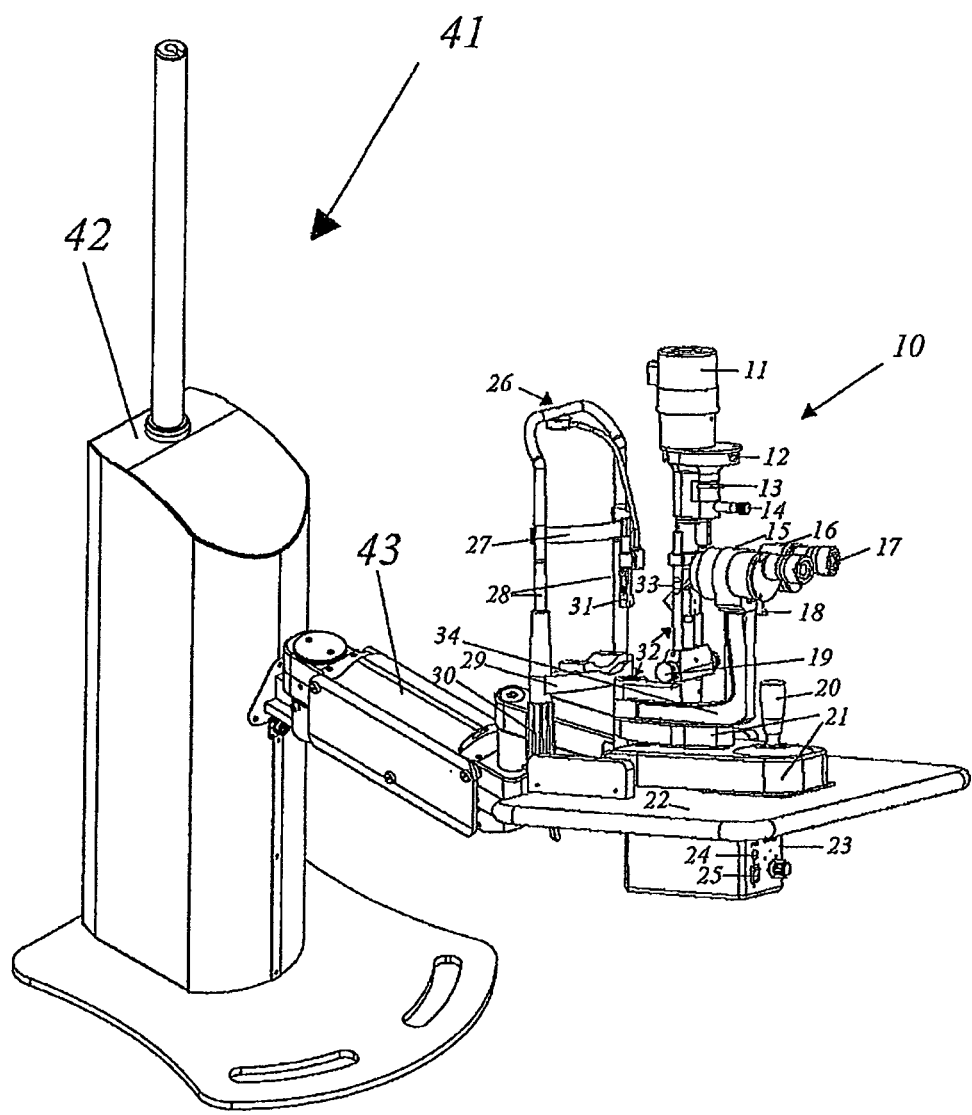
FIG. 3 is a perspective view of the shortened, elevated slit lamp of FIG. 1 placed upon an adjustable instrument stand.

Referring now to FIG. 3, there is shown an adjustable instrument stand 41, including a stand base 42 and instrument arm 43 supporting the slit lamp microscope 10, tabletop 22 and power supply 23.

In more detail, still referring to FIG. 3, the slit lamp microscope 10, tabletop 22 and power supply 23 are mounted on the instrument arm 43 which is connected to the stand base 42. A patient (not shown) is seated on one side of the adjustable instrument stand 41. An examiner (not shown), seated opposite, may raise, lower, push and pull the instrument arm 43 to attain an optimal height and position for examining a patient (not shown) with the slit lamp microscope 10.

Figure 4:
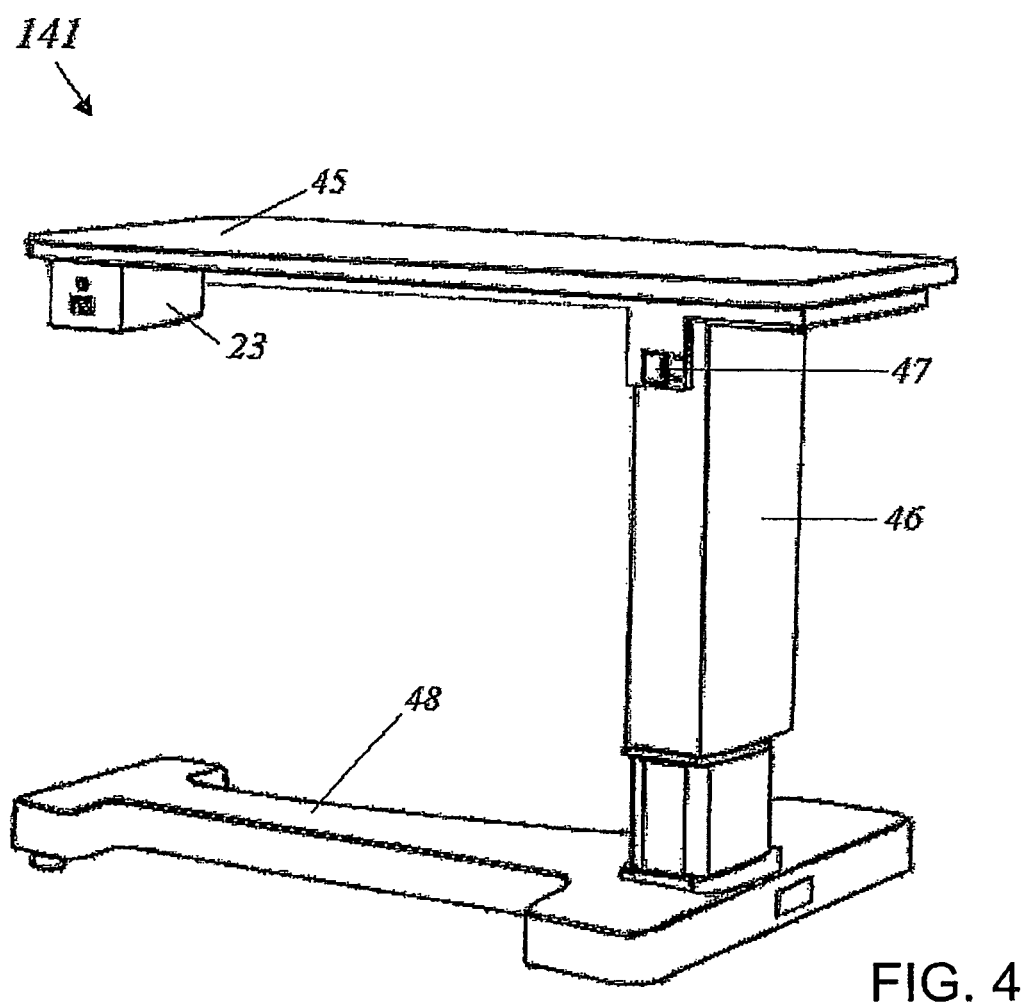
FIG. 4. is a perspective view of an adjustable instrument stand within the present invention.

Referring now to FIG. 4, there is shown an adjustable instrument stand 141 which includes an elongated tabletop 45, adjustable column 46, up/down switch 47 and table base 48.

In more detail, still referring to FIG. 4, the slit lamp microscope 10 (not shown) and power supply 23 may be mounted on the elongated tabletop 45 which is connected to the adjustable column 46 and table base 48. A patient (not shown) is seated on one side of the adjustable instrument stand 141. An examiner (not shown), seated opposite, may raise and lower the adjustable column 46 using the up/down switch 47 to attain an optimal height and position for examining a patient (not shown) with the slit lamp microscope 10.

Figure 5:
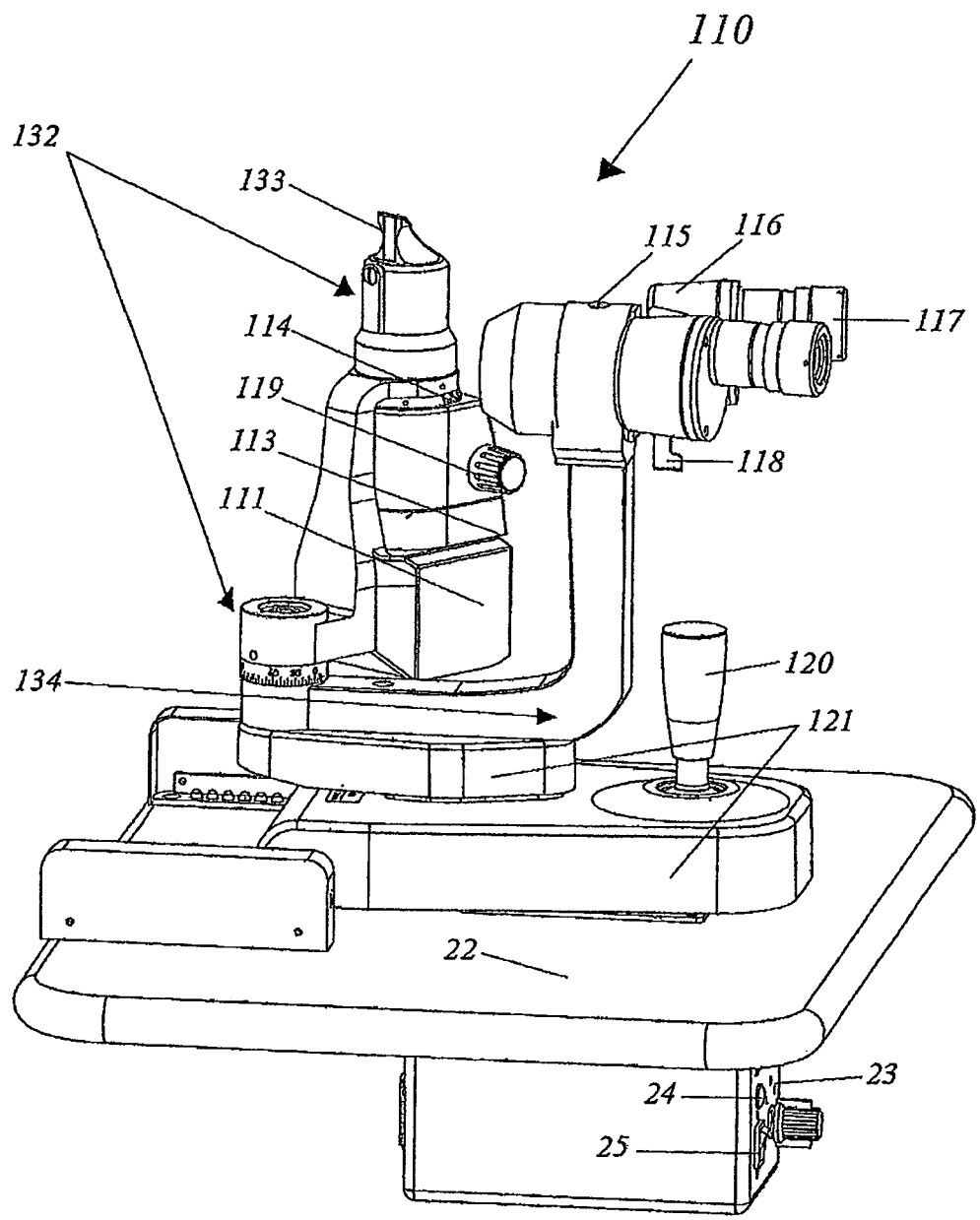
FIG. 5 is a perspective view of a shortened, elevated slit lamp within the present invention.
Figure 7:
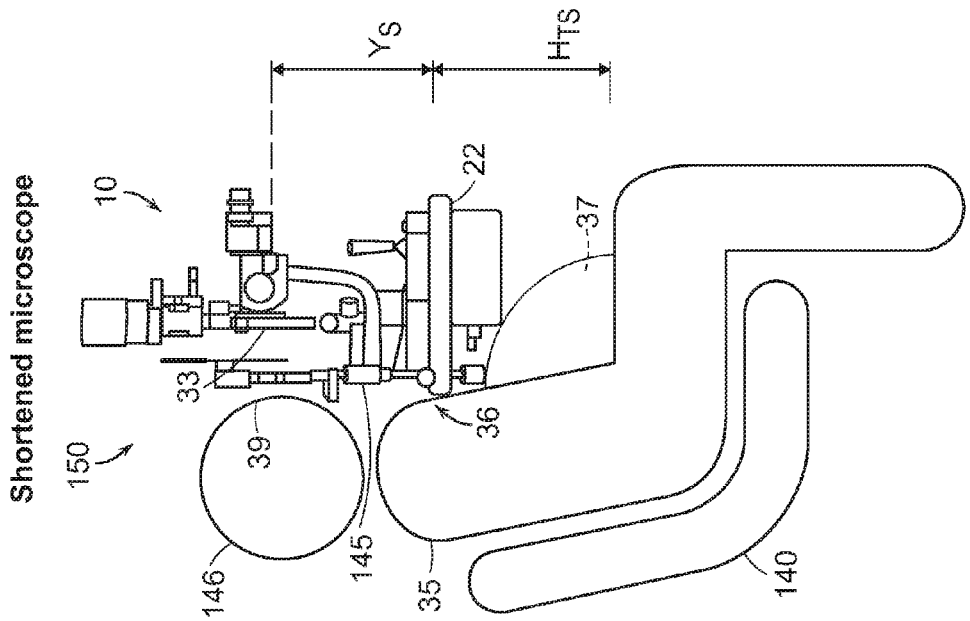
FIG. 7 is a schematic drawing showing an embodiment of an eye examination microscope or device, or slit lamp microscope in the present invention having reduced height, positioned on a table, and the table location relative to the patient's torso raised above the patient's stomach area.

Referring now to FIG. 5, there is shown a slit lamp microscope 110, which includes the lamp cap 111, filter selection lever 113, slit aperture control knob 114, accessories mount 115, prism box 116, examiner's eyepiece 117, magnification changer 118, slit width control knob 119, joystick 120, joystick base 121, illumination tower 132, light reflecting mirror 133 and central ocular arm 134. There is also shown the same tabletop 22, power supply 23, power indicator light 24 and on/off switch 25 as first described in FIG. 1.

In more detail, still referring to FIG. 5, the slit lamp microscope 110 (and all its included parts) is functionally equivalent to the slit lamp microscope 10 first shown in FIG. 1, with the primary difference in construction being the placement of the lamp cap 111 at the bottom of the illumination tower 132 instead of the top.

In further detail, still referring to FIG. 5, the distance (height) between the light reflecting mirror 133 and tabletop 22 is shortened to about 320 mm or less or about 265 mm or less during construction, such as about 260 mm or about 250-255 mm. This shortening may be achieved via a combination of modifications to any or all mechanical parts of the slit lamp, including, without limitation, shrinking, flattening or truncating the illumination tower 132, the central ocular arm 134, and/or the joystick base 121.

The advantages of the present invention include, without limitation, making the slit lamp microscope an accessible and comfortable device for patients of all body shapes, sizes and mobility level without reducing the full functionality and feature set of conventional slit lamp microscopes required by eye care practitioners to provide the highest level of health care.

In broad embodiment, the present invention is a medical examination device with modified mechanical part dimensions for the purpose of improving accessibility and patient comfort.

Figure 6:
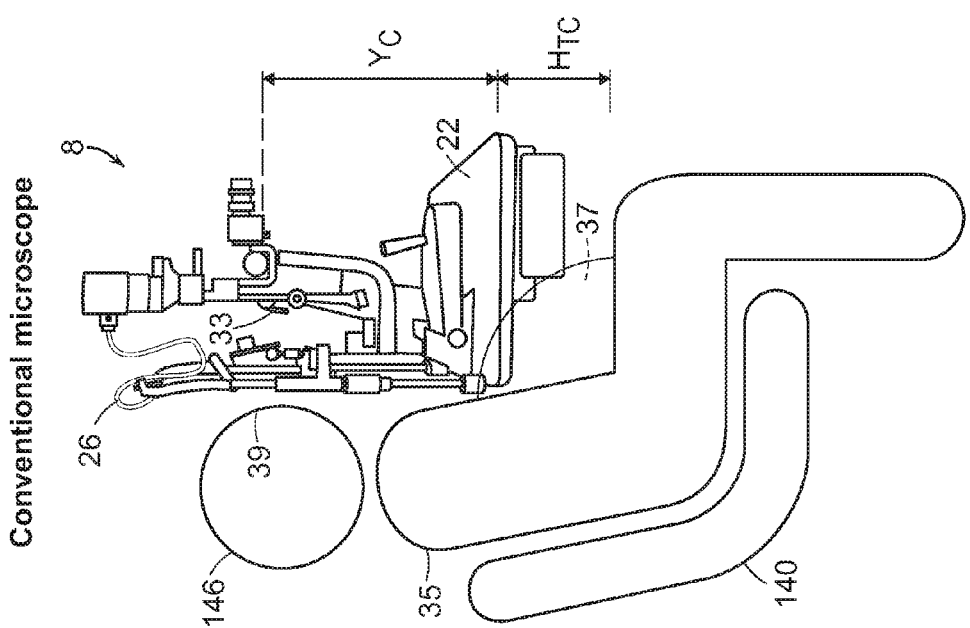
FIG. 6 is a schematic drawing showing a conventional eye examination microscope positioned on a table, and the table location relative to a patient's torso interfering with the patient's stomach region.
Figure 8:
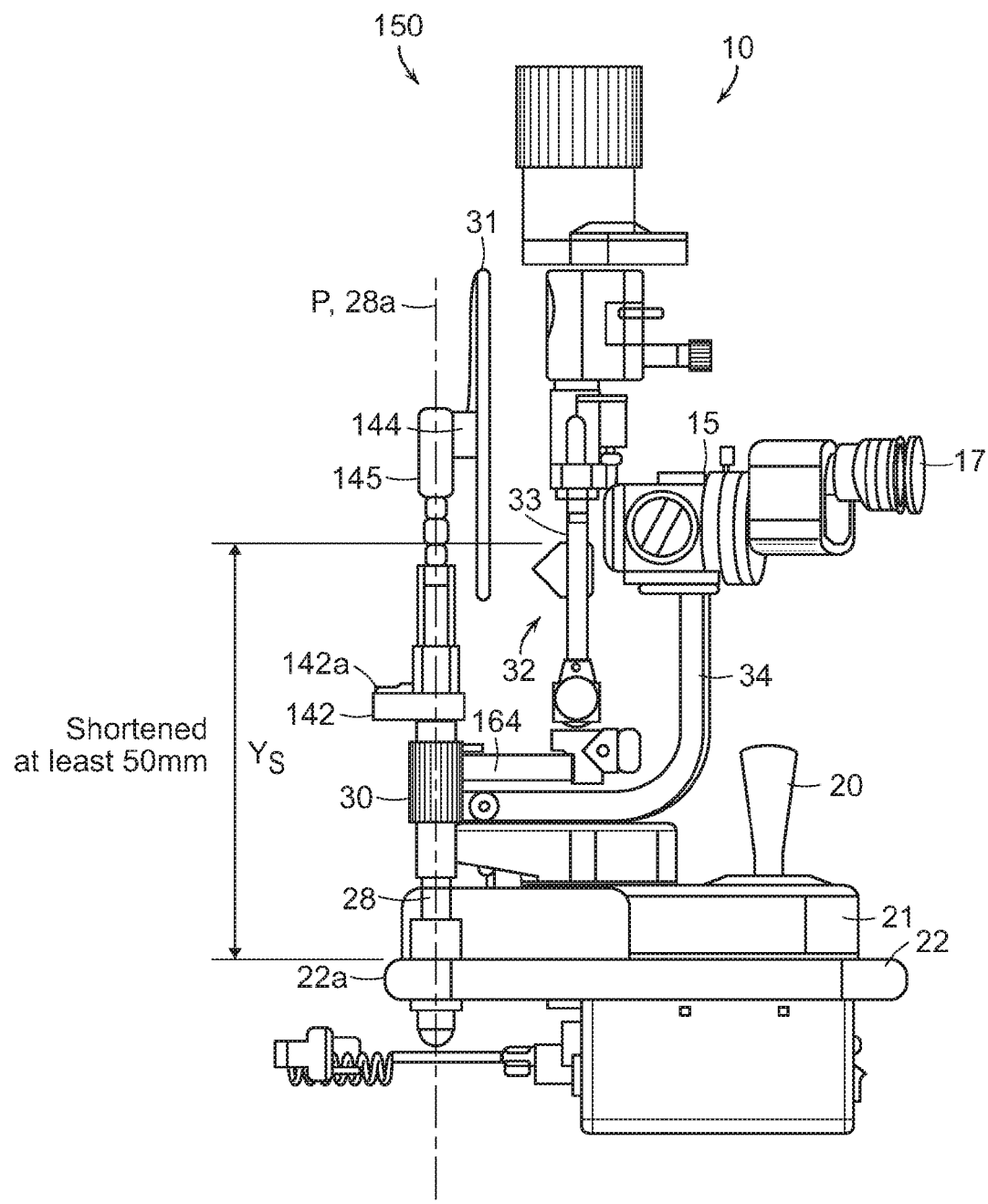
FIG. 8 is a side view of the eye examination device of FIG. 7.
Figure 9:
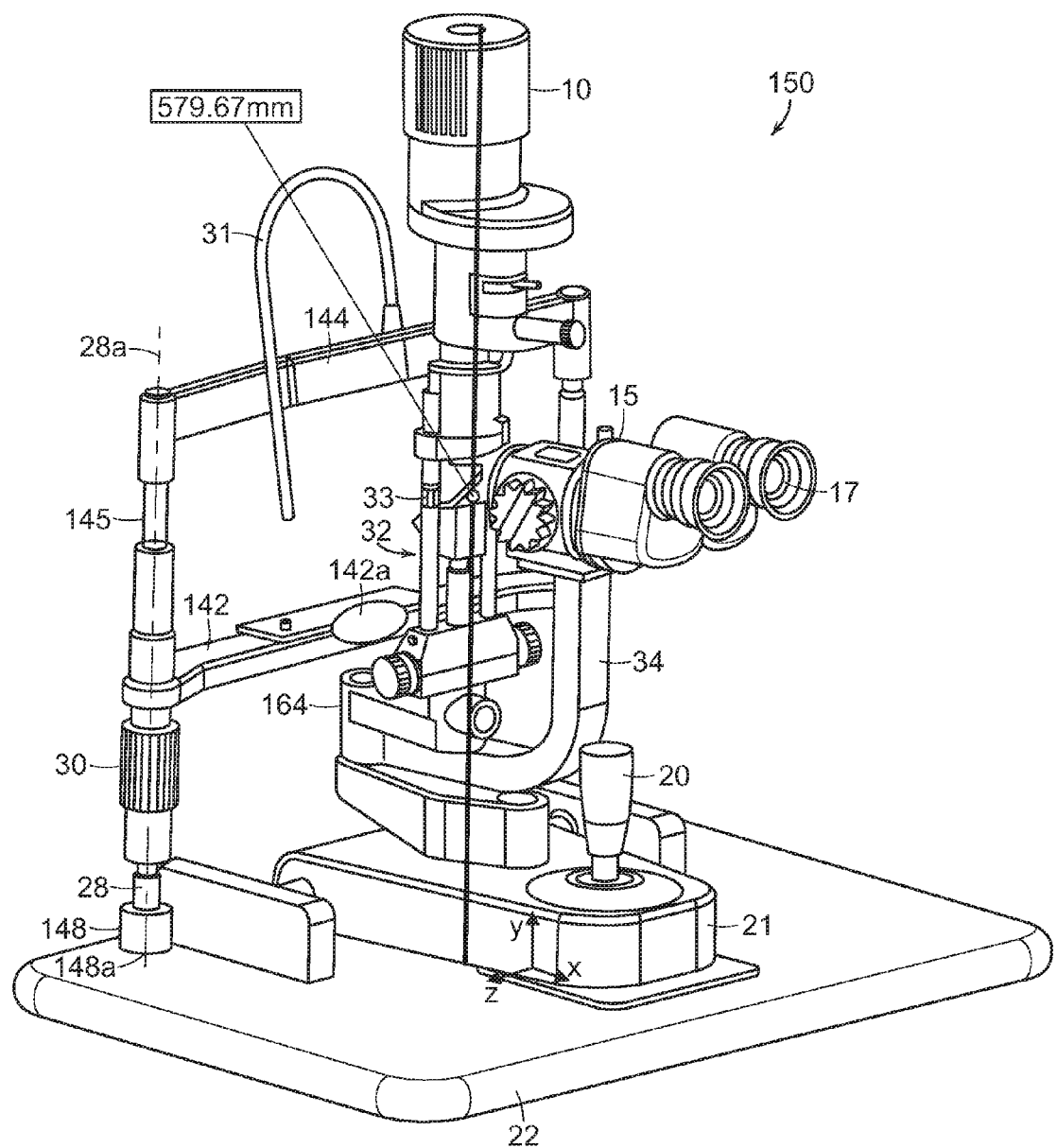
FIG. 9 is a rear perspective view of the eye examination device of FIG. 7.
Figure 10:
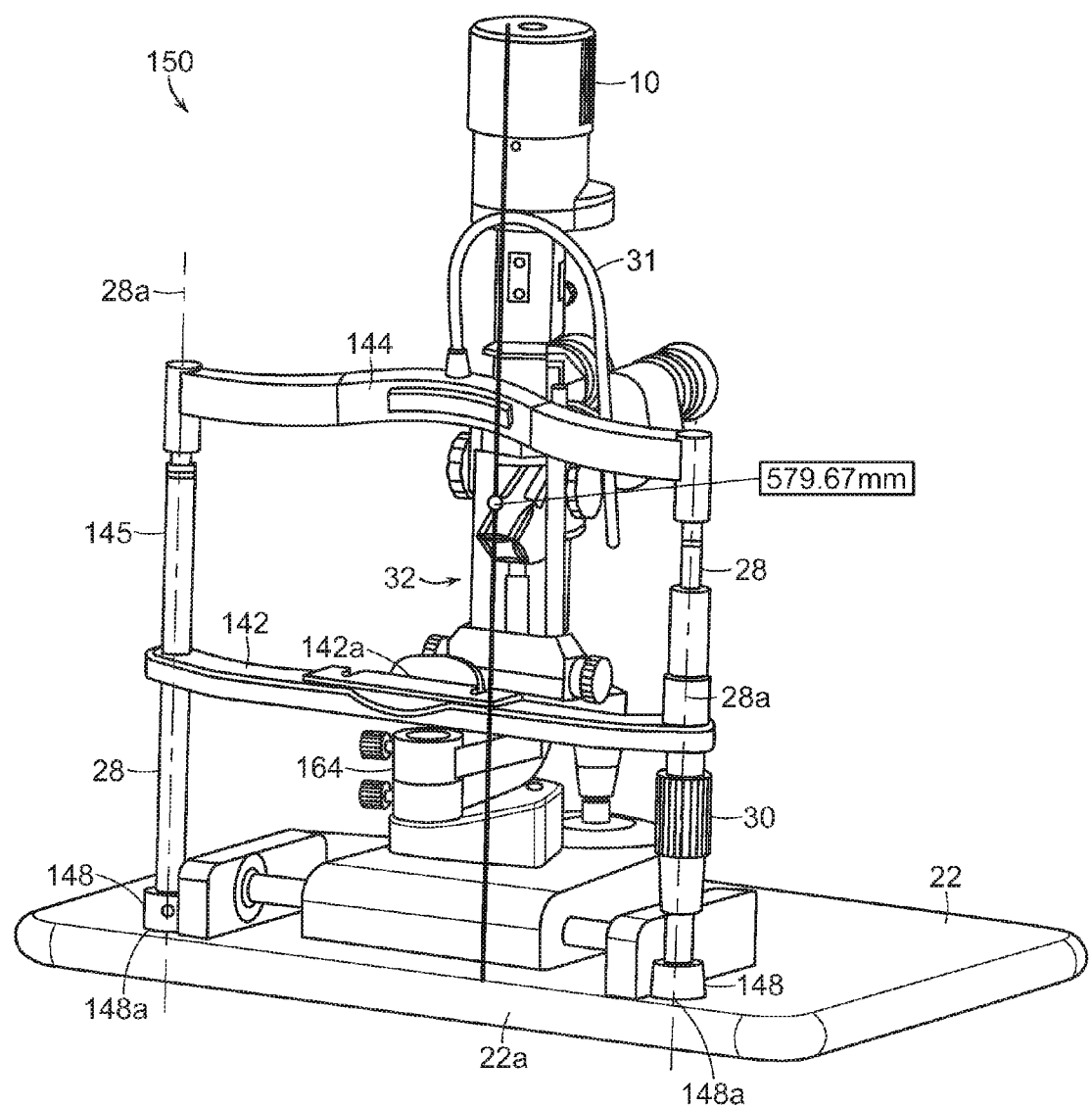
FIG. 10 is a front perspective view of the eye examination device of FIG. 7.

Referring to FIG. 6, in the prior art, a conventional microscope 8 and chin rest set 26 are mounted on top of a table 22. The edge of the table 22 is to be positioned against the lower stomach region 37 of the patient 35 seated in a chair 140, for examining the patient's 35 eyes 39. If the patient 35 is large or obese, such as approaching 200 pounds if short or 300 pounds if average size, the patient's 35 protruding, large, obstructing, interfering or obese body parts or portions such as a protruding lower chest or stomach region 37 will protrude and interfere with the table 22 as shown, which then pushes the table 22 and chin rest set 26 away from the patient 35 making eye examination difficult.

The conventional microscope 8 has a reflecting mirror 33 on the illumination tower which is aligned at about the same level as the patient's 35 eyes 39. The conventional microscope 8 has a distance or height $Y_C$ from the table 22 to the reflecting mirror 33 of typically about 370 mm (14.6 inches), which then positions the table 22 in the area ranging from the lower chest and stomach region 37 of the patient 35 which is at a low height $H_{TC}$ relative to the torso. The total height of the conventional microscope 8 can be about 660 mm (26 inches). In addition to protruding, large, obstructing, interfering or obese lower stomach regions 37, a large or obese patient 35 can also have other protruding, large, obstructing, interfering or obese body portions such as the lower chest parts or breasts which can push the table 22 and chin rest 26 away from the patient 35. Consequently, a large or obese patient's 35 stomach 37 and lower chest parts can push the table 22 away, making eye examination difficult and painful if the patient 35 and table 22 are manually forced together by doctor's assistants to force the patient's 35 head 146 into the chin rest 26.

Referring to FIGS. 7-10, in an embodiment of the present invention, eye examination device 150 can include a shortened slit lamp eye examination microscope 10 having eye examination components with eye examination optics as previously described, mounted to a table 22. The table 22 can be generally rectangular and have a straight or linear forward edge 22a along which a chin rest assembly 145 can be mounted. The joystick base 21, central ocular arm or support member 34, illumination tower, post or structure 32 and/or illumination tower base 164 can be shorter in height than corresponding components in a conventional slit lamp microscope 8. The slit lamp microscope 10 in the present invention can have a shortened distance or height $Y_S$ of about 320 mm (12.5 inches) or less or about 265 mm (10.43 inches or about 10.5 inches) or less, such as about 260 mm or about 250-255 mm, between the light reflecting mirror 33 and the top of the table 22, that is at least about 50 mm (1.69 inches or about 2 inches) shorter than the corresponding height $Y_C$ of conventional slit lamp microscope 8, and in some embodiments can be at least about 100 mm (3.9 inches), 105 mm (4.13 inches), 110 mm (4.3 inches), or 115-120 mm (4.5-4.7 inches) shorter than $Y_C$. Since the light reflecting mirror 33 is aligned at about the same level as the patient's or user's 35 eyes 39 in order to direct light into the eyes, the shorter distance $Y_S$ between the light reflecting mirror 33 and the table 22 raises or positions the table 22 relative to the patient's torso at the upper chest region 36. This position can range from the collarbone region to the chest above protruding large or obese chest or breast body parts of a large or obese patient 35, or around the armpit level, such as for a short person over 200 pounds, and approaching 300 pounds for an average height person. As previously described, the distance between the typical patient's 35 eyes 39 and the upper chest region 36 of the patient is about 320 mm or 265 mm or less, which can be the same distance $Y_S$ between the light reflecting mirror 33 and the table 22 in the present invention. As a result, the table 22 can be positioned above the protruding large or obese body parts of a large or obese patient 35, such as the lower chest or stomach region 37, allowing the straight front or forward edge 22a of table 22 to be pressed or positioned closely against upper chest region 36. Since the large or obese body parts do not interfere with or push the table 22 away from the patient 35, the patient 35 can easily access and position his/her forehand 40 against the forehead rest member or strap 144 and chin and 38 onto the chin rest plate or portion 142a of chin rest member of 142 along the forward edge 22a of table 22 with little or no discomfort. The table 22 can be at a high or elevated height $H_{is}$ relative to the torso of patient 35. In some embodiments, the total height of slit lamp microscope 10 can be about 579.67 mm (22.8 inches) which is about 580 mm.

Referring to FIGS. 9-12, the chin rest assembly 145 in the present invention can also allow for easier and more comfortable acceptance of the patient's 35 forehead 40 and chin 38 than a prior art conventional chin rest 26 (FIG. 11), such as for a large or obese patient 35 such as over 200 pounds and approaching 300 pounds depending on the height.

Referring to FIGS. 11 and 13, in the prior art conventional chin rest 26, the forehead strap 27 and chin rest plate 29 are mounted to the chin rest support bars or posts 28 and extend in a curved manner in the rearward direction away from the posts 28 and the patient 35. As a result, the patient 35 must fit the sides of his/her head 146 through and between the support posts 28 so that the forehead 40 rests against forehead strap 27 and the chin 38 rests on the chin rest plate 29. The sides of patient's 35 head 146 passes through the upright plane P extending between the center axes 28a of support posts 28 to position the patient's chin 38 on the rearward or back side of upright plane P. This can be easily accomplished for a trim or thin person, but as a patient becomes large or obese, such as over 200 pounds for a short person and approaching 300 pounds for an average sized person, the patient's 35 head 146 can have problems properly fitting in the chin rest 26, or can have pain and discomfort when forced therein, since the distance between the support posts 28 is often only 200 mm (7.87 inches).

Referring to FIGS. 8-10, 12 and 14, the chin rest assembly 145 in the present invention can accept and hold or maintain a patient's head 146 in a fixed or stable position. Chin rest assembly 145 can include two spaced apart straight round upright vertical support posts 28 mounted to the table 22 along the linear front or forward edge 22a by respective mounting members or collars 148 that extends through holes 148a in the top of table 22. The support posts 28 can extend upwardly from or near the forward edge 22a of table 22 along respective upright vertical central or center axes 28a and have a central vertical or upright plane P extending between center axes 28a. A forehead rest member or strap 144 can be mounted to and extend between the two support posts 28 at or near the upper regions, ends or tops thereof. The forehead strap 144 can have a curved concave or indented rest portion 144a against which the forehead 40 can rest (FIGS. 18-20). The opposite ends of the forehead strap 144 can have upright or vertical holes or openings 152 along respective upright or vertical axes 152a for engaging and fitting over the ends of support posts 28. The indented rest portion 144a can be positioned between two straight bar portions such that the apex of the curve is near or at the upright plane P extending between the axes 28a of support posts 28. This can position the patient's 35 forehead 40 near or at the upright plane P, so that the sides of the head 146 do not need to pass between the support posts 28. In some embodiments, the apex of the curve of the indented rest portion 144a can be slightly on the rearward side of upright plane P.

A lower chin rest member 142 with a chin rest portion 142a can be movably or adjustably secured to the support posts 28, and spaced below or apart from the upper forehead strap 144. The chin rest member 142 can have opposite ends with upright vertical holes or openings 154 extending therethrough along respective upright or vertical center axes 154a (FIGS. 15-17) for adjustably sliding up and down support posts 28. The chin rest portion 142a can include a concave indentation for accepting the patient's 35 chin 38. The chin rest member 142 can be a planar bar with structural ribs having front or forward 156 and rear or rearward 158 linear or straight edge portions. The opposite distal ends or end portions 168 of the chin rest member 142 can angle forwardly into the front 156 and rear 158 straight edge portions, to extend the front edge portion 156 and chin rest portion 142a forwardly therebetween relative to the axes 154a as well as the upright plane P extending between the center axes 28a of the support posts 28. The rear edge portion 158 can be near or forward of the upright plane P, or axes 28a and 154a. This can position the front edge 156 of the chin rest member 142 forward of the upright plane P and the front edge 22a of the table 22, and chin rest portion 142a forward closer to the patient 35. The chin rest portion 142a can be sized and shaped such that the chin 38 of the patient 35 can be rested on the chin rest portion 142a near or at the upright plane P extending between the axes 28a of support posts 28. As a result, the sides of the patient's 35 head 146 are not required to fit between the support posts 28, so that large heads 146 of a large or obese patient 35 such as around 300 pounds, can be accommodated easily and in comfort with chin rest assembly 145. As can be seen in FIG. 14, generally at most, only the front or front plane of the patient's 35 face 146a coincides with the upright plane P when the patient's 35 forehead 40 and chin 38 engages the indented rest portion 144a and the chin rest portion 142a. The forehead 40, chin 38 and the front of the patient's 35 face 146a can be generally aligned near or along the upright plane P. To provide further clearance, the support posts 28 can be spaced further apart than in chin rest 26. The height of the chin rest member 142 can be raised and lowered with chin rest elevation adjuster 30. A fixation light 31 can be mounted to the forehead strap 144.

Figure 15:
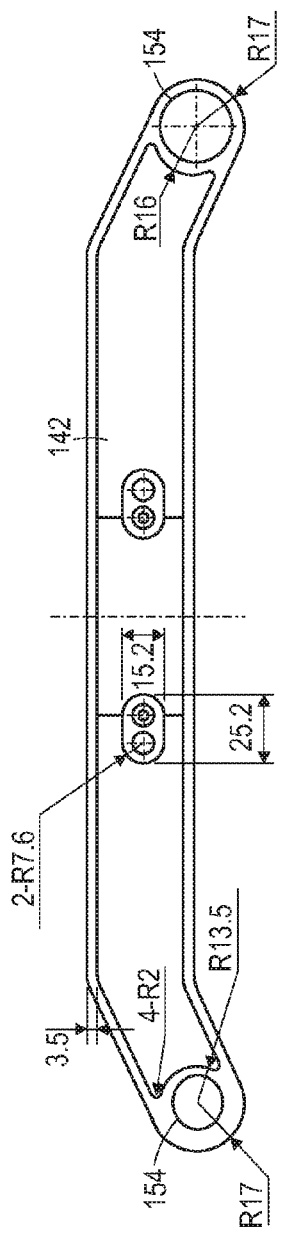
FIGS. 15, 16 and 17 are bottom, side sectional and top views, respectively, of an embodiment of a chin rest member in the present invention.
Figure 16:
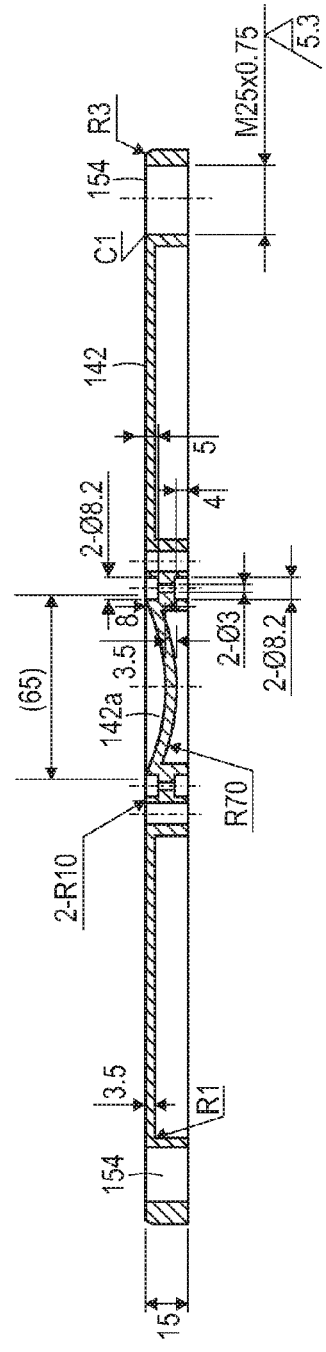
Figure 17:
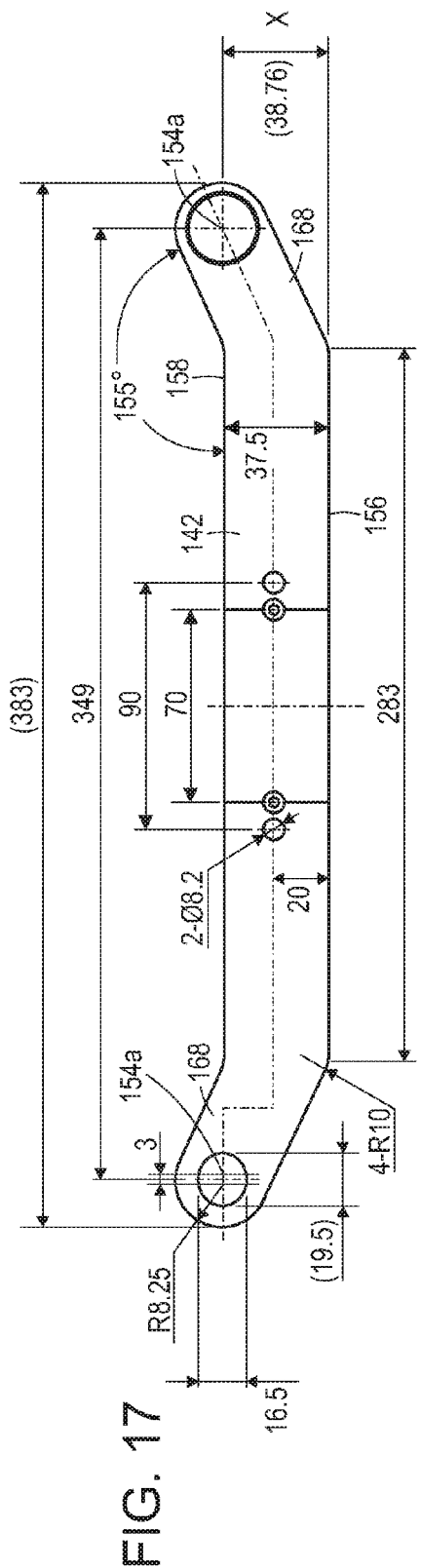

In one embodiment, the support posts 28 can be separated apart from each other about 349 mm (13.74 inches) or greater between center axes 28a. In some embodiments, the support posts 28 can have a diameter of about 19 mm (0.75 inches). Referring to FIGS. 15-20, embodiments of the forehead strap 144 and chin rest member 142 can have respective holes 152 and 154 which are spaced apart the same distance or dimension for mounting on support posts 28. Chin rest member 142 can be about 383 mm (15 inches) long, about 15 mm (0.59 inches) thick, and about 37.5 mm (1.48 inches) wide. The end portions 168 can be angled about 155° relative to the rear edge 158 and, the front edge 156 can extend the distance X of about 38.76 mm (1.53 inches) forward of axes 154a. This can extend the chin rest portion 142a and front edge 156 forwardly relative to the upright plane P and axes 28a by at least about 38.76 or 38 mm. The front linear edge 156 of the chin rest member 142 can extend about 263 mm (10.35 inches) between the two forwardly angled ends 168. Further dimensions are shown in FIGS. 15-17. In some embodiments, the front edge 156 can extend the distance X of at least about 18 mm (0.7 inches) forward of axes 154a, or at least about 30 mm (1.18 inches) forward of axes 154a.

The forehead strap 144 can be about 369 mm (14.53 inches) long and about 53.15 mm (2.1 inches) high. Further dimensions are shown in FIGS. 18-20.

Figure 22:
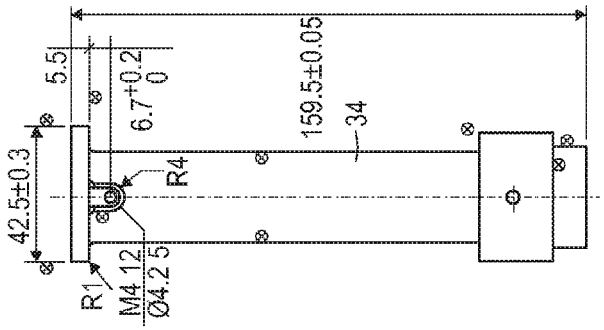
FIGS. 21, 22 and 23 are side with portions in section, front and top views, respectively, of an embodiment of a central ocular arm in the present invention.
Figure 21:
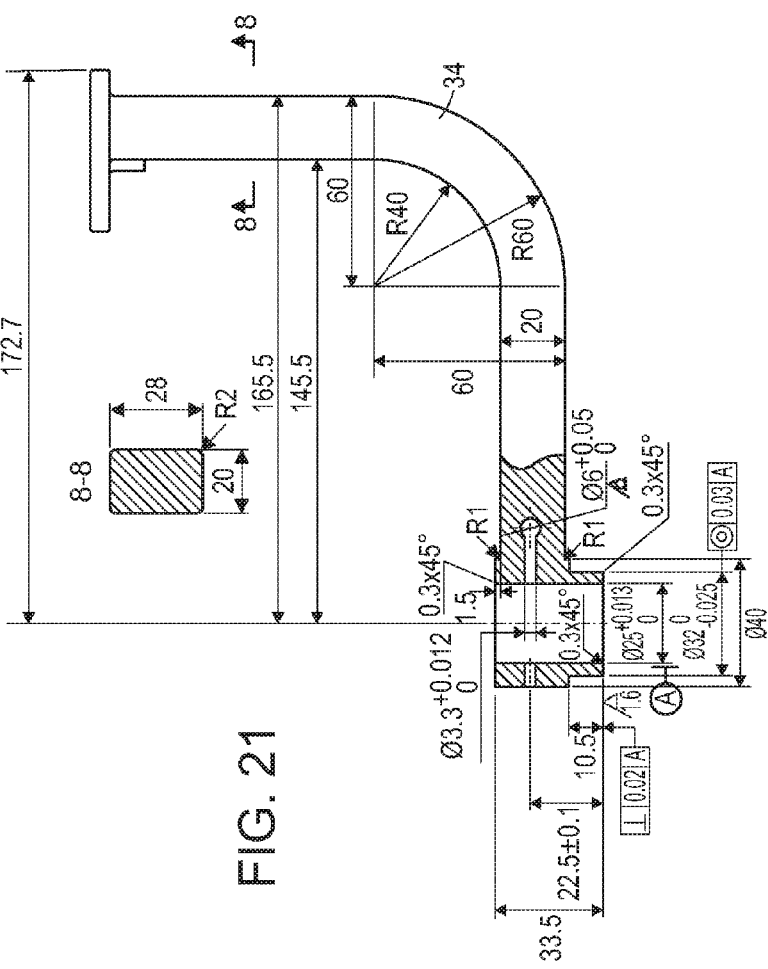
Figure 23:
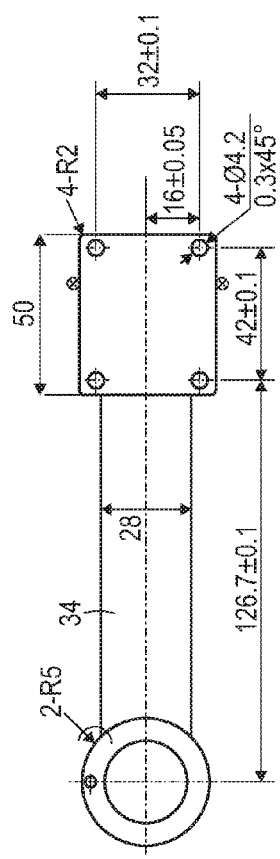

FIGS. 21-23 show dimensions for an embodiment of the central ocular arm 34, including height, width, thickness and diameters. FIGS. 24-28 show dimensions for an embodiment of the illumination tower base 164, including height, width, length and diameters.

Figure 29:
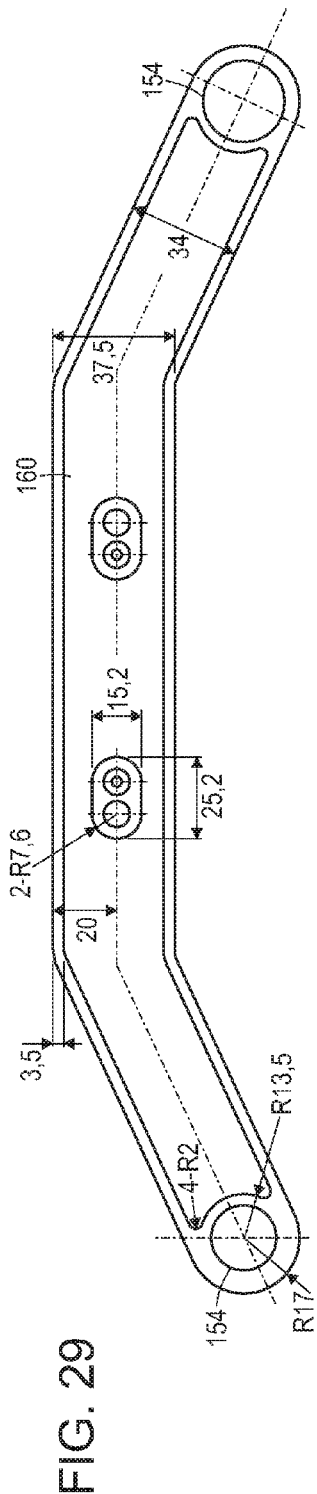
FIGS. 29, 30 and 31 are bottom, side sectional and top views, respectively, of another embodiment of a chin rest member in the present invention.
Figure 30:
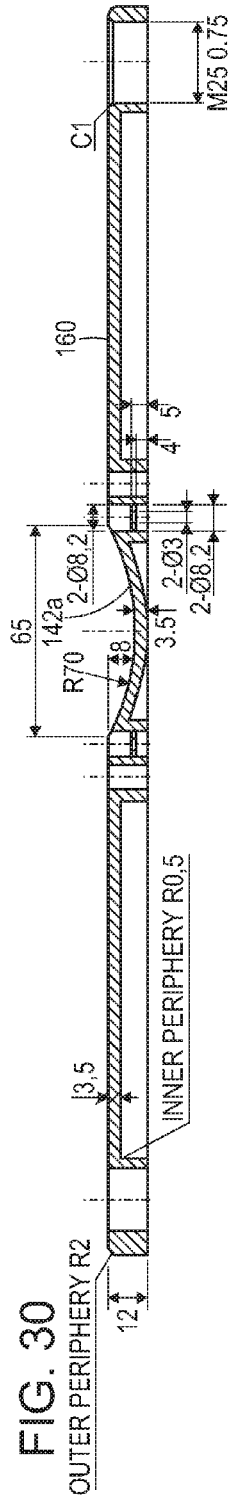
Figure 31:
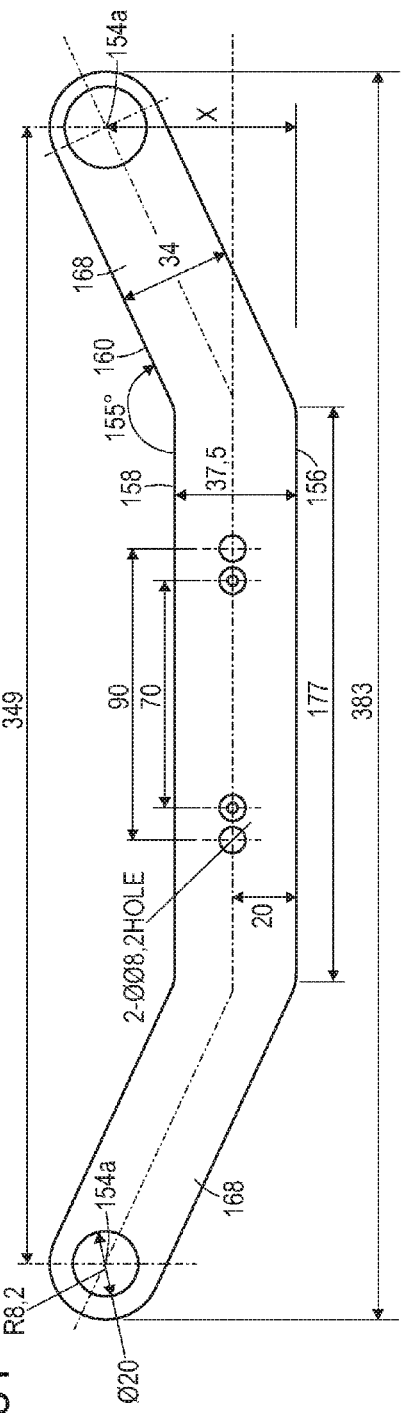
Figures 38, 39, 41:
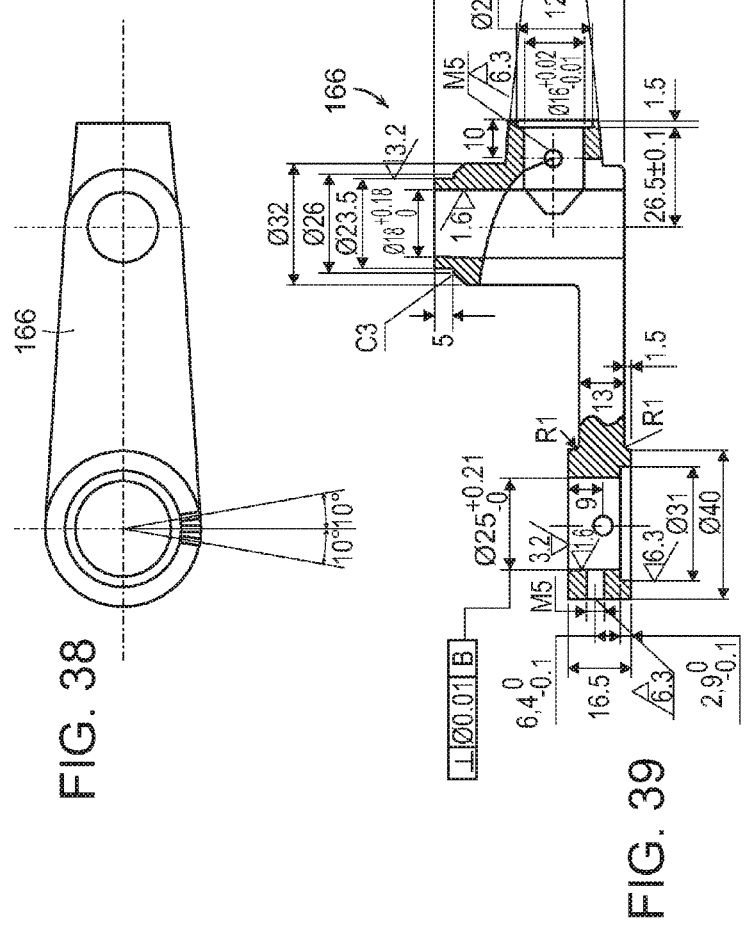
FIGS. 38, 39, 40, 41 and 42 are top, side with portions in section, end, bottom and enlarged detail views, respectively, of an embodiment of another illumination tower base in the present invention.
Figure 40:
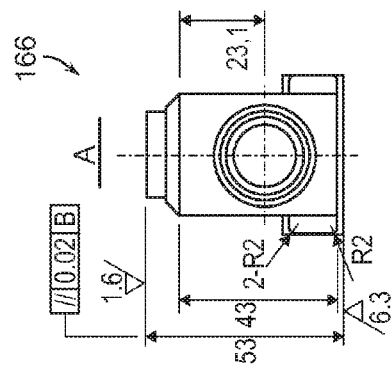
Figure 42:
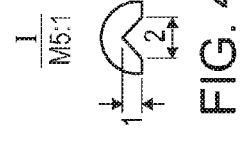

FIGS. 29-42 depict other embodiments of a chin rest member 160, forehead rest member or strap 155, central ocular arm 162 and illumination tower base 166, which can be used instead of those in FIGS. 15-28. The embodiment of the chin rest member 160 can differ from chin rest member 142 in that the forward edge 156 can be shorter and positioned further forwardly of axes 154a in view that the opposite distal ends 168 are longer and angle further forwardly. The front edge 156 can be about 177 mm (7 inches) long and extend a distance X of about 69.6 mm (2.74 inches) or 70 mm forward of axes 154a. This can extend the front edge 156 and chin rest portion 142a forwardly relative to the upright plane P and axes 28a by about 69.6 mm or 70 mm, which can position the patient's 35 chin 38 and head 146 forwardly of the front edges or surfaces of the support posts 28 so that the head 146 is supported in front thereof in a cantilevered or offset location or manner relative to the vertical axes 28a, upright plane P and support posts 28. The chin rest member 160 can be about 12 mm thick (0.47 inches). Extending the chin rest portion 142a further forwardly towards the patient 35 and away from the table 22 and support posts 28, can make chin rest member 160 more usable and comfortable for large or obese patients around 400 pounds. The dimensions can be found on FIGS. 29-31.

The embodiment of forehead rest strap 155 in FIGS. 32-34 can differ from forehead strap 144 in that the curved concave rest portion 144a can be shallower with less curvature. The opposite distal ends of the forehead strap 155 can be angled forwardly to position the apex of the curve of the indented rest portion 144*a* forward of axes 152*a*, 28*a* and the upright plane P extending between axes 28*a* of support posts 28. This can position the patient's 35 forehead 40 forwardly of the front edges or surfaces of the support posts 28 in alignment with the chin 38 resting on chin rest member 160. As a result, the chin 38, the forehead 40 and the whole head 146 do not have to pass through or between posts 28, and the head 146 is supported in a cantilevered or offset manner relative to vertical axes 28*a*, upright plane P and support posts 28. In addition, the height can be less. The dimensions can be found on FIGS. 32-34.

Various embodiments of the chin rest assembly 145, forehead rest members 144 and 155, and chin rest members 142 and 160, and various dimensions thereof, can be employed in the present invention, so that the sides of the patient's 35 head 146 do not need to pass between the support posts 28. Moving the front edge 156 and the chin rest portion 142*a* forwardly away from the axes 154*a*, 28*a* and upright plane P, from about 38 mm to 70 mm (or in other embodiments about 18 or 30 to 70 mm), can move the front or front plane of the patient's face 146*a* from a location at most generally coinciding with the upright plane P, to locations being forwardly spaced apart away from the upright plane P, and in front of the support posts 28. Intermediate dimensions X for the chin rest members can be employed. The support posts 28 by being straight and vertical, and mounted through the table 22, can support the heavy weight of an obese patient 35 with little or no deflection when the head 146 is supported by the chin rest assembly 145. Deflection of the chin rest assembly is not desired because that can move or vary the position of the eyes 39 during examination. The support posts 28, forehead rest members 144/155 and chin rest members 142/160, can be made of plastics or metals, such as steel or aluminum, or combinations and portions thereof.

FIGS. 35-37 show dimensions for another embodiment of the central ocular arm 162 which can be used with chin rest member 160 and forehead strap 155. FIGS. 38-42 show dimensions for another embodiment of an illumination tower base 166 with which can be also used with chin rest member 160 and forehead strap 155.

While this invention has been particularly shown and described with references to example embodiments thereof, it will be understood by those skilled in the art that various changes in form and details may be made therein without departing from the scope of the invention encompassed by the appended claims. For example, certain dimensions given can often vary +/−10 mm, +/−15 mm, and +/−30 mm. Additionally, other suitable dimensions or shapes can be used for the components. Various components can be combined or omitted. Although embodiments of the present invention have been described with respect to large or obese patients, normal sized patients or patients with physical limitations, conditions or disabilities can also use such embodiments.

What is claimed is:

1. An eye examination device comprising:
    eye examination optics for examining a patients eyes mounted to a table, the table having a straight forward edge on the patient's side, in which height of eye examination components including the eye examination optics is shortened, so that lower chest and stomach regions of the patient can be positioned below the table during examination in a non-interfering manner, the eye examination components includes a joystick base mounted to the table, a central ocular arm having a horizontal bottom portion and an upright upper portion mounted on the joystick base, with an optical assembly being mounted to the upright upper portion of the central ocular arm, and an illumination tower having a light source mounted to the horizontal bottom portion of the central ocular arm having a light reflecting mirror adjacently spaced apart from the optical assembly for reflecting light from the light source onto the patient's eye, the light reflecting mirror for being level with the patient's eye and being positioned above the table 320 mm or less so that the table is positioned level with the patient's upper chest region; and
    a chin rest assembly for accepting the patient's head and maintaining the patient's head in a fixed stable position, the chin rest assembly comprising two spaced apart upright posts spaced at least 349 mm apart and extending along parallel upright axes secured to the table inwardly from the straight forward edge, with a forehead rest member being secured to the two upright posts at an upper region and a chin rest member being secured to the two upright posts below the forehead rest member, the chin rest member having a chin rest portion which extends forwardly towards the patient at least 18 mm relative to an upright plane extending between centers of the two upright posts and away from the eye examination optics, so that at most, only a front of the patient's face coincides with the upright plane when the patient's head engages the chin rest portion.

2. An eye examination device comprising:
    a table having a straight forward edge on a patient's side; and
    eye examination optics for examining the patient's eyes mounted on top of the table, eye examination components including the eye examination optics having a shortened height above the table so that lower chest and stomach regions of the patient can be positioned below the table during examination in a non-interfering manner, the eye examination components including an illumination tower having a light source and a light reflecting mirror for reflecting light from the light source onto the patient's eye, the light reflecting mirror for being level with the patient's eye and being positioned above the table 320 mm or less so that the table is positioned level with the patient's upper chest region; and
    a chin rest assembly for accepting the patient's head and maintaining the patient's head in a fixed stable position, the chin rest assembly comprising two spaced apart upright posts spaced at least 349 mm apart and extending along parallel upright axes secured to the table inwardly from the straight forward edge, with a forehead rest member being secured to the two upright posts at an upper region and a chin rest member being secured to the two upright posts below the forehead rest member, the chin rest member having a chin rest portion which extends forwardly towards the patient at least 18 mm relative to an upright plane extending between centers of the two upright posts and away from the eye examination optics, so that at most, only a front of the patient's face coincides with the upright plane when the patient's head engages the chin rest portion.

3. The device of claim 2 in which the chin rest member comprises a bar having two ends that are angled forwardly to extend the chin rest portion forwardly therebetween.

4. The device of claim 3 in which the chin rest portion extends forwardly relative to the upright plane by at least 38 mm.

5. The device of claim 4 in which the chin rest portion extends forwardly relative to the upright plane from 38 mm to 70 mm.

6. The device of claim 2 in which the eye examination components includes a joystick base mounted to the table, a central ocular arm having a horizontal bottom portion and an upright upper portion mounted on the joystick base, with an optical assembly being mounted to the upright upper portion of the central ocular arm, and the illumination tower having the light source mounted to the horizontal bottom portion of the central ocular arm having the light reflecting mirror adjacently spaced apart from the optical assembly for reflecting light from the light source onto the patient's eye, the light reflecting mirror for being level with the patient's eye and being positioned above the table 265 mm or less so that the table is positioned level with the patient's upper chest region.

7. A method of examining a patient's eyes comprising:
using eye examination optics on top of a table having a straight forward edge on the patient's side and examining the patient's eyes,
the height of eye examination components including the eye examination optics mounted on top of the table being shortened, so that lower chest and stomach regions of the patient are positioned below the table in a non-interfering manner, the eye examination components includes an illumination tower having a light source and a light reflecting mirror for reflecting light from the light source onto the patient's eye, the light reflecting mirror for being level with the patient's eye and being positioned above the table 320 mm or less so that the table is positioned level with the patient's upper chest region; and
accepting the patient's head and maintaining the patient's head in a fixed stable position with a chin rest assembly, the chin rest assembly comprising two spaced apart upright posts spaced at least 349 mm apart and extending along parallel upright axes secured to the table inwardly from the straight forward edge, with a forehead rest member being secured to the two upright posts at an upper region and a chin rest member being secured to the two upright posts below the forehead rest member, the chin rest member having a chin rest portion which extends forwardly towards the patient at least 18 mm relative to an upright plane extending between centers of the two upright posts and away from the eye examination optics, so that at most, only a front of the patient's face coincides with the upright plane when the patient's head engages the chin rest portion.

8. The method of claim 7 further comprising:
providing the eye examination components with a joystick base mounted to the table, a central ocular arm having a horizontal bottom portion and an upright upper portion mounted on the joystick base, with an optical assembly mounted to the upright upper portion of the central ocular arm, and the illumination tower having the light source mounted to the horizontal bottom portion of the central ocular arm having the light reflecting mirror adjacently spaced apart from the optical assembly for reflecting light from the light source onto the patient's eye; and
positioning the light reflecting mirror level with the patient's eye and above the table 265 mm or less so that the table is positioned level with the patient's upper chest region.

9. The method of claim 7 further comprising providing the chin rest member with a bar having two ends that are angled forwardly to extend the chin rest portion forwardly therebetween.

10. The method of claim 7 further comprising extending the chin rest portion forwardly relative to the upright plane by at least 38 mm.

11. The method of claim 10 further comprising extending the chin rest portion forwardly relative to the upright plane from 38 mm to 70 mm.

\* \* \* \* \*